United States Patent [19]

Cotrel et al.

[11] 4,016,274
[45] Apr. 5, 1977

[54] NAPHTHYRIDINE DERIVATIVES

[75] Inventors: Claude Cotrel, Paris; Cornel Crisan, Sceaux; Claude Jeanmart, Brunoy (Essonne); Mayer Naoum Messer, Bievres (Essone), all of France

[73] Assignee: Rhone-Poulenc S.A., Paris, France

[22] Filed: Oct. 17, 1975

[21] Appl. No.: 623,359

Related U.S. Application Data

[63] Continuation-in-part of Ser. No. 469,431, May 13, 1974, abandoned.

[30] Foreign Application Priority Data

May 15, 1973 France .............................. 73.17516
Mar. 14, 1974 France .............................. 74.08728
Mar. 14, 1974 France .............................. 74.08730

[52] U.S. Cl. ........................ 424/250; 260/268 BC
[51] Int. Cl.² ...................................... C07D 401/14
[58] Field of Search .............. 260/268 BC; 424/250

[56] References Cited

OTHER PUBLICATIONS

Challier et al., Chemical Abstracts, vol. 77, 114, 432n (1972).
Cotrel et al., Chemical Abstracts, vol. 77, 5526a (1972).

*Primary Examiner*—Donald G. Daus
*Assistant Examiner*—Jose Tovar
*Attorney, Agent, or Firm*—Stevens, Davis, Miller & Mosher

[57] ABSTRACT

Compounds of the formula:

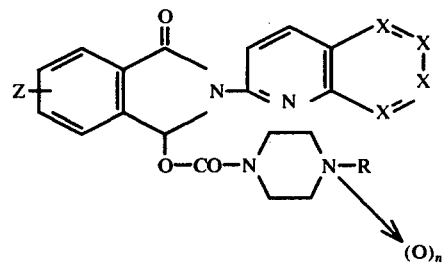

wherein one of the symbols =X— represents =N— and the other three each represent a group

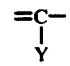

in which Y represents hydrogen, halogen, alkyl, alkoxy, cyano or nitro, at least two of the symbols representing hydrogen, Z represents hydrogen, halogen, alkyl, alkoxy, trifluoromethyl or nitro, and (i) $n$ represents zero and R represents hydrogen, alkyl, alkenyl, alkynyl, hydroxyalkyl or phenyl, or (ii) $n$ represents 1 and R represents alkyl, hydroxyalkyl or phenyl, are new compounds possessing pharmacological properties; they are particularly active as tranquilizers and anti-convulsant agents.

29 Claims, No Drawings

NAPHTHYRIDINE DERIVATIVES

This application is a Continuation-in-Part of our application Ser. No. 469,431 filed May 13th, 1974 and now abandoned.

This invention relates to new therapeutically useful naphthyridine derivatives, to processes for their preparation and pharmaceutical compositions containing them.

The new naphthyridine derivatives of the present invention are those of the general formula:

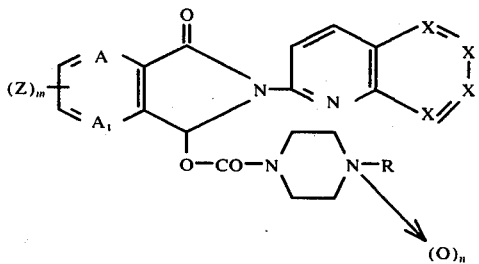

wherein one of the symbols =X— represents =N— and the other three each represent a group

in which Y represents a hydrogen or halogen (preferably chlorine or bromine) atom, an alkyl radical containing 1 to 4 carbon atoms (preferably methyl), an alkoxy radical containing 1 to 4 carbon atoms (preferably methoxy), or a cyano or nitro radical, the symbols =A— and =$A_1$— represent a group =CH— or =N—, =$A_1$— representing a group =CH— or =N— when =A— represents =CH— and =$A_1$— representing =N— when A represents =N—, the symbol Z represents a hydrogen or halogen atom, an alkyl or alkoxy radical containing 1 to 4 carbon atoms, the nitro radical or the trifluoromethyl radical, $m$ represents zero or an integer from 1 to 4 (preferably zero), and (i) $n$ represents zero and R represents a hydrogen atom, an alkyl radical containing 1 to 4 carbon atoms (e.g. ethyl, isopropyl, t.-butyl or, more especially, methyl), an alkenyl radical containing 2 or 4 carbon atoms (e.g. allyl), an alkynyl radical containing 2 to 4 carbon atoms (e.g. propargyl), a hydroxyalkyl radical containing 1 to 4 carbon atoms (e.g. 2-hydroxy-ethyl) or a phenyl radical, or (ii) $n$ represents 1 and R represents an alkyl or hydroxyalkyl radical containing 1 to 4 carbon atoms, or a phenyl radical, and acid addition salts thereof. It is to be understood that the symbols X of the three groups

represented by symbol X in the above formula may represent the same or different atoms or radicals as stated above, and when symbol $m$ represents the integer 2, 3 or 4 the atoms or radicals attached to the carbon atoms of the ring may be the same or different.

According to a feature of the invention, the compounds of general formula I wherein $n$ represents zero are prepared by the process which comprises reacting a chlorocarbonylpiperazine of the general formula:

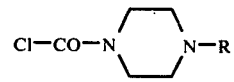

(wherein R represents a hydrogen atom or an alkyl, alkenyl, alkynyl, hydroxyalkyl or phenyl radical) with a naphthyridine derivative of the general formula:

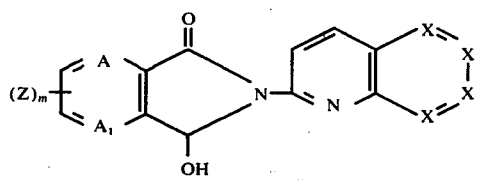

wherein X, A, $A_1$, Z and $m$ are as hereinbefore defined.

Generally, a compound of general formula II is reacted with an alkali metal salt, optionally prepared in situ, of a compound of general formula III, the reaction being carried out in an anhydrous organic solvent, e.g. dimethylformamide or tetrahydrofuran, at a temperature below 60° C.

The reaction can also be carried out by reacting an acid addition salt of a compound of general formula II, preferably the hydrochloride, with a compound of general formula III, working in pyridine and optionally in the presence of a tertiary amine (e.g. triethylamine) which liberates the compound of general formula II from its salt.

The naphthyridine derivatives of general formula III can be obtained by partial reduction of an imide of the general formula:

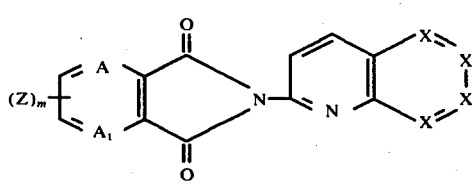

(wherein X, A, $A_1$, Z and $m$ are as hereinbefore defined) to convert one of the carbonyl groups to a hydroxy-methylene group.

The reduction is generally carried out by means of an alkali metal borohydride in organic or aqueous-organic solution, such as a mixture of dioxan and methanol or a mixture of dioxan and water or a mixture of methanol and water of a mixture of ethanol and water.

The partial reduction of an imide of general formula IV can lead to isomeric products which can be separated by physico-chemical methods such as fractional crystallisation or chromatography.

The imides of general formula IV can be prepared by reacting a 2-aminonaphthyridine of the general formula:

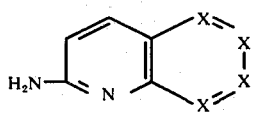

V (wherein X is as hereinbefore defined) with an anhydride of the general formula:

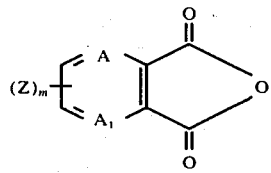

VI (wherein A, A₁, Z and m are as hereinbefore defined), optionally forming as an intermediate a product of the general formula:

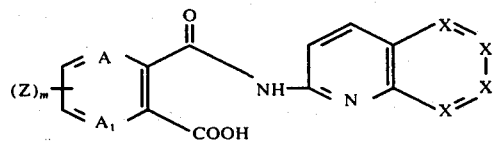

VII wherein X, A, A₁, Z and m are as hereinbefore defined.

The reaction of the 2-aminonaphthyridine of general formula V with the anhydride of general formula VI is generally carried out by heating in an organic solvent, for example acetic acid, dimethylformamide, acetonitrile or diphenyl ether.

The cyclisation of the intermediate product of general formula VII to form an imide product of general formula IV can generally be effected either by heating with acetyl chloride in acetic acid or acetic anhydride, or by the action of a condensation agent such as N,N'-dicyclohexylcarbodiimide in dimethylformamide at a temperature of about 20° C.

Alternatively the naphthyridine derivatives of general formula III may be made by cyclizing an amide of the formula:

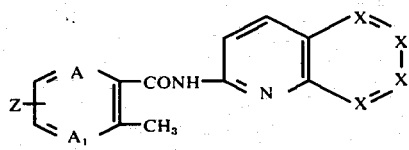

VIII by treatment with N-bromosuccinimide in the presence of azodiisobutyronitrile or an acetal diester in an aqueous organic medium.

It is also possible to make naphthyridines of general formula III from other naphthyridines of the same general formula by converting a derivative in which Z has one value into a derivative in which Z has a different value. For example a derivative in which Z is hydrogen may be nitrated to give a derivative in which Z is nitro and the latter may be converted into a derivative in which Z is halogen via the corresponding amino and diazonium derivatives.

According to another feature of the invention, the compounds of general formula I wherein n is zero or 1 and R has the corresponding meanings given above are prepared by the process which comprises reacting a piperazine of the general formula:

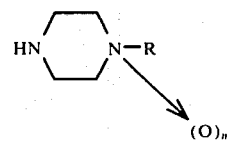

IX (wherein n is zero or 1 and R is as hereinbefore defined) with a mixed carbonate of the general formula:

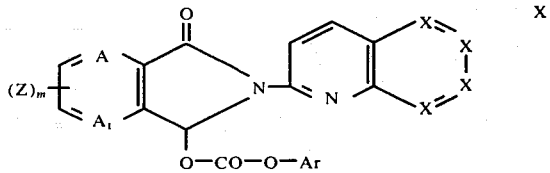

X wherein X, A, A₁, Z and m are as hereinbefore defined, and Ar represents a phenyl radical optionally substituted by an alkyl radical containing 1 to 4 carbon atoms or a nitro radical. The reaction is generally carried out in an anhydrous organic solvent, e.g. acetonitrile or dimethylformamide, at a temperature of about 20° C., e.g. 15° to 25° C.

The piperazine compound of general formula IX wherein n represents 1 and R represents the methyl radical and its dihydrochloride can be obtained by oxidation of t.-butyl (4-methylpiperazin-1-yl)carboxylate by means of 4-nitroperbenzoic acid in anhydrous chloroform at a temperature not exceeding 40° C., followed by replacement of the t.-butoxy-carbonyl group by a hydrogen atom by heating 1-methyl-4-t.-butoxycarbonyl-piperazine-1 -oxide hydrochloride under reflux in an ethanolic medium in the presence of anhydrous hydrochloric acid. The other piperazine compounds of general formula IX can be obtained in a similar manner.

The mixed carbonates of general formula X can be prepared by reacting a chloroformate of the general formula:

Cl — CO — O — Ar     XI (wherein Ar is as hereinbefore defined) with a naphthyridine derivative of general formula III. The reaction is generally carried out in a basic organic solvent, e.g. pyridine, at a temperature between 0° and 20° C.

According to another feature of the invention, the compounds of general formula I wherein n represents 1 and R represents an alkyl, hydroxyalkyl or phenyl radical are obtained by the process which comprises the oxidation of a corresponding compound of general formula I wherein n represents zero and R is as defined above. The oxidation is generally carried out by means of a organic peracid, e.g. 3-chloroperbenzoic acid or 4-nitroperbenzoic acid, in an organic solvent. e.g. chloroform, and at a temperature of about 20° C.

The naphthyridine derivatives of general formula I obtained by the aforementioned processes can be purified by physical methods such as distillation, crystallisation or chromatography, or by chemical methods such as the formation of salts, crystallisation of the salts and decomposition of them in an alkaline medium. In carrying out the said chemical methods and nature of the anion of the salt is immaterial, the only requirement being that the salt must be well-defined and readily crystallisable.

The naphthyridine derivatives of general formula I may be converted by methods known per se into acid addition salts. The acid addition salts may be obtained by the action of acids on the naphthyridine derivatives in appropriate solvents. As organic solvents there may be used alcohols, ethers, ketones or chlorinated hydrocarbons. The salt which is formed is precipitated, if necessary after concentration of the solution, and is isolated by filtration or decantation.

The naphthyridine derivatives of the invention and their acid addition salts possess valuable pharmacological properties; they are particularly active as tranquilisers and anti-convulsant agents. In animals (mice) they have proved active as such at doses of between 0.1 and 100 mg./kg. animal body weight when administered orally, in particular in the following tests:

i. electric battle test according to a technique similar to that of Tedeschi et al. [J. Pharmacol., 125, 28 (1959)], ii. convulsion with pentetrazole according to a technique similar to that of Everett and Richards [J. Pharmacol., 81, 402 (1944)], iii. supramaximal electroshock according to the technique of Swinyard et al [J. Pharmacol., 106, 319 (1952)], and iv. locomotor activity according to the technique of Courvoisier [Congres des Medecins, Alienistes et Neurologistes- Tours - (8/13th June 1959)] and Julou (Bulletin de la Societe de Pharmacie de Lille, No. 2, Jan. 1967, p. 7).

Furthermore, they exhibit only low toxicity; their 50% lethal dose ($LD_{50}$) in the case of mice is generally greater than 300 mg./kg. animal body weight when administered orally.

The naphthyridine derivatives of the general formula:

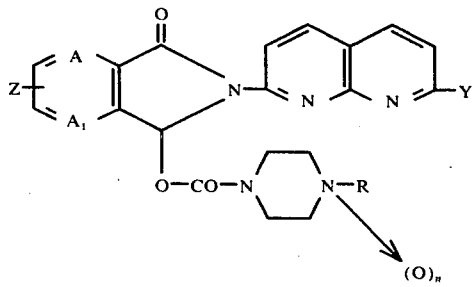

XII wherein Y represents hydrogen, halogen, preferably fluorine, chlorine, or bromine, alkyl of 1 through 4 carbon atoms, preferably methyl, alkoxy of 1 through 4 carbon atoms, preferably methoxy, or cyano, =A— and =$A_1$— represent a group =CH— or =N—, =$A_1$— representing =CH— or =N— when =A— represents =CH— and $A_1$ representing =N— when =A— represents =N— (both A and $A_1$ preferably representing =N—), Z represents hydrogen, halogen, preferably fluorine, chlorine or bromine, alkoxy of 1 through 4 carbon atoms, preferably methoxy, nitro or trifluoromethyl and n represents zero and R represents an alkyl radical containing 1 to 4 carbon atoms (preferably methyl), an alkenyl radical containing 2 to 4 carbon atoms, an alkynyl radical containing 2 to 4 carbon atoms or a hydroxyalkyl radical containing 1 to 4 carbon atoms, or n represents 1 and R represents the methyl radical, and their acid addition salts, are of very particular interest. Of outstanding value are the compounds 2-(7-bromo-1,8-naphthyridin-2-yl)-3-(4-methyl-piperazin-1-yl)-carbonyloxy-isoindolin-1-one, 2-(7-cyano-1,8-naphthyridin-2-yl)-3-(4-methylpiperazin-1-yl)carbonyloxy-isoindolin-1-one, 2-(7-chloro-1,8-naphthyridine-2-yl)-3-[4-(2-hydroxyethyl)-piperazin-1-yl]carbonyloxy-isoindolin-1-one, 3-(4-allylpiperazin-1-yl)carbonyloxy-2-(7-chloro-1,8-naphthyridin-2-yl)isoindolin-1-one, 2-(7-chloro-1,8-naphthyridin-2-yl)-3-(4-ethylpiperazin-1-yl)carbonyloxy-isoindolin-1-one, 2-(7-chloro-1,8-naphthyridin-2-yl)-3-(4-propargylpiperazin-1-yl)carbonyloxy-isoindolin-1-one, 2-(7-chloro-1,8-naphthyridin-2-yl)-3-(4-t.-butylpiperazin-1-yl)carbonyloxy-isoindolin-1-one, 4- [2-(7-chloro-1,8-naphthyridin-2-yl)-3-oxo-isoindolin-1-yl]oxycarbonyl -1-methylpiperazine-1-oxide, 6-(7-chloro-1,8-naphthyridin-2-yl)-5-(4-methylpiperazin-1-yl)carbonyloxy-7-oxo-6,7-dihydro-5H-pyrrolo[3,4-b]pyrazine, 2-(7-chloro-1,8-naphthyridin-2-yl)-5-fluoro-3-(4-methyl-piperazinyl)-carbonyloxy-1-isoindolinone, 2-(7-chloro-1,8-naphthyridin-2-yl)-3-(4-methyl-piperazinyl)-carbonyloxy-5-nitro-1-isoindolinone, 2-(7-chloro-1,8-naphthyridin-2-yl)-5-methoxy-3-(4-methyl-piperazinyl)-carbonyloxy-1-isoindolinone, 2-(7-chloro-1,8-naphthyridin-2-yl)-3-(4-methyl-piperazinyl)-carbonyloxy-6-nitro-1-isoindolinone, 4-chloro-2-(7-chloro-1,8-naphthyridin-2-yl)-3-(4-methyl-piperazinyl)-carbonyloxy-1-isoindolinone, 7-chloro-2-(7-chloro-1,8-naphthyridin-2-yl)-3-(4-methyl-piperazinyl)-carbonyloxy-1-isoindolinone, 6-bromo-2-(7-chloro-1,8-naphthyridin-2-yl)-3-(4-methyl-piperazinyl)-carbonyloxy-1-isoindolinone, 6-chloro-2-(7-chloro-1,8-naphthyridin-2-yl)-3-(4-methyl-1-piperazinyl)-carbonyloxy-1-isoindolinone, 2-(7-chloro-1,8-naphthyridin-2-yl)-3-[4-(2-methyl-prop-2-en-1-yl)-1-piperazinyl]carbonyloxy-1-isoindolinone, 3-[4-(but-2-en-1-yl)-1-piperazinyl]-carbonyloxy-2-(7-chloro-1,8-naphthyridin-2-yl)-1-isoindolinone, 3-[4-(but-3-en-1-yl)-1-piperazinyl]-carbonyloxy-2-(7-chloro-1,8-naphthyridin-2-yl)-1-isoindolinone, 2-(7-fluoro-1,8-naphthyridin-2-yl)-3-(4-methyl-piperazinyl)-carbonyloxy-1-isoindolinone, 2-(7-chloro-1,8-naphthyridin-2-yl)-3-(4-methyl-piperazinyl)-carbonyloxy-5-trifluoromethyl-1-isoindolinone, 2-(7-chloro-1,8-naphthyridin-2-yl)-3-(4-methyl-piperazinyl)-carbonyloxy-6-trifluoromethyl-1-isoindolinone and, more especially, 2-(7-chloro-1,8-naphthyridin-2-yl)-3-(4-methyl-piperazin-1-yl)carbonyloxy-isoindolin-1-one, and their acid addition salts.

For therapeutic purposes, the naphthyridine derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of naphthyridine derivatives of this invention.

EXAMPLE 1

Sodium hydride (50% dispersion in mineral oil) (2.1 g.) is added all at once to a suspension of 2-(7-chloro-1,8-naphthyridin-2-yl)-3-hydroxy-isoindolin-1-one (12.4 g.) in anhydrous dimethylformamide (125 cc.), whilst cooling externally with an ice bath. When the evolution of gas has ceased, a solution of 1-chlorocarbonyl-4-methyl-piperazine (11.3 g.) in anhydrous dimethylformamide (110 cc.) is added, the external cooling being maintained. After the end of the addition, the reaction mixture is stirred for 14 hours at 0° C., and then for 6 hours at 22° C. The reaction mixture is then poured onto ice (800 g.). The product which crystallises is filtered off, washed with water (240 cc.) and dried in air to yield a crude product (13 g.) which melts at about 210° C. On recrystallisation from acetonitrile (900 cc.), 2-(7-chloro-1,8-naphthyridin-2-yl)-3-(4-methylpiperazin-1-yl)carbonyloxy-isoindolin-1-one (8.5 g.), melting at 204° C., is obtained.

2-(7-Chloro-1,8-naphthyridin-2-yl)-3-hydroxy-isoindolin-1-one can be prepared by adding potassium borohydride (1.72 g.) to a suspension of 2-(7-chloro-1,8-naphthyridin-2-yl)phthalimide (17.7 g.) in dioxan (87 cc.) and a saturated aqueous solution of disodium phosphate (26.4 cc.), whilst cooling externally with an ice bath. After stirring for 14 hours, the mixture is allowed to return to a temperature of about 20° C., stirring is carried out for a further 2 hours, and then a saturated aqueous solution of disodium phosphate (400 cc.) is added. The precipitate which forms is filtered off and washed with cold water (225 cc.). After drying in air, 2-(7-chloro-1,8-naphthyridin-2-yl)-3-hydroxy-isoindolin-1-one (17.5 g.), melting at 248° C., is obtained.

2-(7-Chloro-1,8-naphthyridin-2-yl)phthalimide can be prepared by heating a mixture of 2-(7-hydroxy-1,8-naphthyridin-2-yl)phthalimide (26.3 g.) with phosphorus oxychloride (79 cc.) and dimethylformamide (3.5cc.) under reflux until the evolution of gas ceases. After cooling, the reaction mixture is poured into ice-water (650 cc.) without exceeding 25° C. The product obtained is filtered off, washed with water (150 cc.) and dried to constant weight to give 2-(7-chloro-1,8-naphthyridin-2-yl)phthalimide (24.1 g.) melting at 268° C.

2-(7-Hydroxy-1,8-naphthyridin-2-yl)phthalimide can be prepared by heating a mixture of 2-amino-7-hydroxy-1,8-naphthyridine (25 g.) with phthalic anhydride (70 g.) in acetic acid (1,400 cc.) under reflux for 3 hours. After cooling, an insoluble material is filtered off. The crystals obtained are filtered off, washed successively with diethyl ether (60 cc.), water (90 cc.), a saturated solution of sodium bicarbonate (120 cc.) and finally water (60 cc.). The crystals are dried to constant weight and 2-(7-hydroxy-1,8-naphthyridin-2-yl)phthalimide (17 g.), melting at 370° C., is thus obtained.

2-Amino-7-hydroxy-1,8-naphthyridine can be prepared according to the method described by S. Carboni et al, Gazz. Chim. Ital., 95, 1498 (1965).

EXAMPLE 2

Triethylamine (5.6 cc.) followed by anhydrous pyridine (25 cc.) are added to a suspension of 2-(7-chloro-1,8-naphthyridin-2-yl)-3-hydroxy-isoindolin-1-one (3.12 g.) and 1-chlorocarbonyl-4-methylpiperazine hydrochloride (5.97 g.) in methylene chloride (50 cc.), whilst keeping the temperature at about 25° C. The reaction mixture is then heated at a temperature of about 50° C. for 1 hour and is then stirred for 18 hours at a temperature of about 20° C. Methylene chloride (50 cc.) and water (100 cc.) are then added. The aqueous layer is decanted and then washed three times with methylene chloride (50 cc.). The organic layers are combined and washed with water (50 cc.), dried over anhydrous sodium sulphate and then concentrated to dryness under reduced pressure. On recrystallisation of the resulting residue from acetonitrile (100 cc.), 2-(7-chloro-1,8-naphthyridin-2-yl)-3-(4-methylpiperazin-1-yl)carbonyloxy-isoindolin-1-one (2.5 g.), melting at 203° C., is obtained.

EXAMPLE 3

A suspension of sodium hydride (50% dispersion in mineral oil) (1.46 g.) in anhydrous dimethylformamide (80 cc.) is added to a suspension of 3-hydroxy-2-(1,5-naphthyridin-2-yl)isoindolin-1-one (7 g.) in anhydrous dimethylformamide (410 cc.). When the evolution of gas has ceased, a solution of 1-chlorocarbonyl-4-methyl-piperazine (4.6 g.) in anhydrous dimethylformamide (25 cc.) is added dropwise. After stirring for 4 hours, the reaction mixture is poured into water (3,000 cc.) cooled to 13° C. The precipitate is filtered off, washed with water (75 cc.) and then dried to yield 3-(4-methyl-piperazin-1-yl)carbonyloxy-2-(1,5-naphthyridin-2-yl)isoindolin-1-one (5.7 g.) melting at 170°–171° C. After recrystallisation from acetonitrile (50 cc.), the products melts at 173° C.

3-Hydroxy-2-(1,5-naphthyridin-2-yl)isoindolin-1-one can be prepared by adding potassium borohydride (0.91 g.) to a suspension of 2-(1,5-naphthyridin-2-yl)-phthalimide (6.2 g.) in dioxan (57 cc.) and a saturated aqueous solution of disodium phosphate (11.1 cc.) cooled to 10° C. The mixture is then allowed to return to a temperature of about 20° C. After 2 hours, a saturated aqueous solution of disodium phosphate (105 cc.) is added. The precipitate is filtered off, washed with distilled water (300 cc.) and then dried to yield 3-hydroxy-2-(1,5-naphthyridin-2-yl)iscindolin-1-one (4.8 g.) melting at 208° C.

2-(1,5-Naphthyridin-2-yl)phthalimide can be prepared by heating 2-amino-1,5-naphthyridine (20 g.) with phthalic anhydride (20.4 g.) in dimethylformamide (138 cc.) for 40 minutes at 145° C. After cooling, distilled water (550 cc.) is added. The precipitate is filtered off and then washed with water (150 cc.). 2-(1,5-Naphthyridin-2-yl)phthalimide (17.5 g.), melting at 206° C., is thus obtaied.

2-Amino-1,5-naphthyridine can be prepared according to W. Czuba, Rec. Trav. Chim., 82, 988 (1963).

EXAMPLE 4

Sodium hydride (50% dispersion in mineral oil) (0.8 g.) is added to a suspension of 2-(7-methoxy-1,8-naphthyridin-2-yl)-3-hydroxy-isoindolin-1-one (4.63 g.) in anhydrous dimethylformamide (45 cc.), whilst keeping the temperature between 18°–20° C. The reaction mixture is stirred for a further 4 hours 30 minutes. A solution of 1-chlorocarbonyl-4-methylpiperazine (2.7 g.) in anhydrous dimethylformamide (25 cc.) is then added over the course of 15 minutes and at a temperature of 20° C. The suspension is stirred for 17 hours at a temperature of about 20° C., and then anhydrous hexamethylphosphotriamide (7 cc.) is added. After 15 minutes, the reaction mixture is poured into ice-water (500 g.). The precipitate is filtered off and washed with water (45 cc.). A product (6.1 g.) is obtained and is recrystallised from diisopropyl ether (1,500 cc.). 2-(7-Methoxy-1,8-naphthyridin-2-yl)-3-(4-methylpiperazin-1-yl)carbonyloxy-isoindolin-1-one (3 g.), melting at 191° C., is thus obtained.

The 2-(7-methoxy-1,8-naphthyridin-2-yl)-3-hydroxy-isoindolin-1-one can be prepared in the following way: Preparation of 2-acetylamino-7-chloro-1,8-naphthyridine, m.p. 251°–253° C., according to S. Carboni et al [Gazz. Chim. Ital., 95, 1492 (1965)]. Preparation of 2-amino-7-methoxy-1,8-naphthyridine (1.0 g.), m.p. 156° C., by reacting sodium methoxide (1.8 g.) with 2-acetylamino-7-chloro-1,8-naphthyridine (2.2 g.) in anhydrous methanol (40 cc.) under reflux for 45 minutes. Preparation of 2-(7-methoxy-1,8-naphthyridin-2-yl)-phthalimide (20 g.), m.p. 295° C., by reacting phthalic anhydride (10 g.) with 2-amino-7-methoxy-1,8-naphthyridine (12 g.) in diphenyl ether (240 cc.) for 10 minutes at 160° C. Preparation of 2-(7-methoxy-1,8-naphthyridin-2-yl)-3-hydroxy-isoindolin-1-one (18.6 g.), m.p. 218° C., by reacting potassium borohydride (3.55 g.) with 2-(7-methoxy-1,8-naphthyridin-2-yl)phthalimide (20 g.) in dioxan (200 cc.) and a saturated aqueous solution of disodium phosphate (40 cc.) for 4 hours at a temperature of about 20° C.

EXAMPLE 5

The procedure described in Example 4 is followed but starting with 2-(7-bromo-1,8-naphthyridin-2-yl)-3-hydroxy-isoindolin-1-one (8 g.) in anhydrous dimethylformamide (240 cc.), sodium hydride (50% dispersion in mineral oil) (1.2 g.) and 1-chlorocarbonyl-4-methylpiperazine (4.1 g.) in anhydrous dimethylformamide (40 cc.). After stirring at 26° C. for 18 hours, the reaction mixture is poured into ice-water (1,500 cc.). The insoluble matter (7.3 g.) is filtered off and dissolved in a mixture (73 cc.) of methylene chloride and ethyl acetate (80–20 by volume). The solution obtained is passed through a column of silica gel (73 g.). Elution is first carried out with a mixture (5,750 cc.) of methylene chloride and ethyl acetate (80-20 by volume); the corresponding eluates are discarded. Elution is then carried out with pure ethyl acetate (1,250 cc.) and then with a mixture (1,250 cc.) of ethyl acetate and methanol (50—50 by volume); the corresponding eluates are combined and concentrated to dryness. A residue (3 g.) is obtained which is dissolved in ethanol (90 cc.). A solution of oxalic acid (0.53 g.) in ethanol (10.5 cc.) is added to the solution obtained. The mixture is stirred for 1 hour and the precipitate which forms is filtered off and washed with ethanol (6 cc.). A product (1.8 g.), melting at 260° C., is thus obtained and is treated with a saturated solution of sodium bicarbonate (50 cc.) and methylene chloride (40 cc.). The organic layer is isolated by decanting, dried over anhydrous potassium carbonate and concentrated to dryness. A residue weighing 1.2 g. is obtained and is recrystallised from ethanol (80 cc.). 2-(7-Bromo-1,8-naphthyridin-2-yl)-3-(4-methylpiperazin-1-yl)carbonyloxy-isoindolin-1-one (0.9 g.), melting at 225°–230° C., is thus obtained.

2-(7-Bromo-1,8-naphthyridin-2-yl)-3-hydroxyisoindolin-1-one can be prepared in the following way: Preparation of 2-(7-bromo-1,8-naphthyridin-2-yl)phthalimide (23.6 g.), m.p. 265° C., by heating a mixture of 2-(7-hydroxy-1,8-naphthyridin-2-yl)phthalimide (20.5 g.) and phosphorus pentabromide (30.3 g.) in bromoform (205 cc.) and dimethylformamide (7 cc.) for 1 hour at a temperature of about 100° C.

Preparation of 2-(7-bromo-1,8-naphthyridin-2-yl)-3-hydroxy-isoindolin-1-one (8.2 g.), m.p. 264° C., from 2-(7-bromo-1,8-naphthyridin-2-yl)phthalimide (10.6 g.) and potassium borohydride (1.2 g.) in a mixture (200 cc.) of methanol and dioxan (50—50 by volume) at a temperature of about 20° C.

EXAMPLE 6

Following the procedure of Example 4 but starting with 2-(7-cyano-1,8-naphthyridin-2-yl)-3-hydroxy-isoindolin-1-one (4.7 g.), sodium hydride (50% dispersion in mineral oil) (1.5 g.), 2-chlorocarbonyl-4-methylpiperazine (5.04 g.), anhydrous tetrahydrofuran (97 cc.) and anhydrous hexamethylphosphotriamide (25 cc.), a crude product (5.7 g.) is obtained which is then dissolved in methylene chloride (100 cc.). The resulting solution is passed through a column of silica gel (57 g.). Elution is carried out successively with methylene chloride (2,400 cc.), ethyl acetate (1,400 cc.) and then a mixture (200 cc.) of ethyl acetate and methanol (50—50 by volume), collecting 200 cc. fractions. The last eight fractions are combined and concentrated to dryness. The residue, weighing 3.4 g., is recrystallised from acetonitrile (250 cc.) to yield 2-(7-cyano-1,8-naphthyridin-2-yl)-3-(4-methylpiperazin-1-yl)carbonyloxy-isoindolin-1-one (2.6 g.) melting at 266°–268° C.

2-(7-Cyano-1,8-naphthyridin-2-yl)-3-hydroxy-isoindolin-1-one can be prepared in the following way: Preparation of 2-(7-cyano-1,8-naphthyridin-2-yl)phthalimide (7.3 g.), m.p. 320° C., by heating 2-(7-bromo-1,8-naphthyridin-2-yl)phthalimide (17.7 g.) with cuprous cyanide (9 g.) in nitrobenzene (177 cc.) at 160°–165° C. for 1 hour. Insoluble matter is removed by carrying out a hot filtration and the filtrate is then cooled. The product which crystallises is filtered off and then recrystallised from dimethylformamide (70 cc.). Preparation of 2-(7-cyano-1,8-naphthyridin-2-yl)-3-hydroxy-isoindolin-1-one (4.7 g.), m.p. 260° C., from 2-(7-cyano-1,8-naphthyridin-2-yl)phthalimide (5.8 g.) and sodium borohydride (1.04 g.) in methanol (290 cc.) at a temperature between 23° and 27° C.

EXAMPLE 7

Following the procedure of Example 4 but starting with 2-(1,6-naphthyridin-2-yl)-3-hydroxy-isoindolin-1-one (1.7 g.) in anhydrous tetrahydrofuran (17 cc.), sodium hydride (50% dispersion in mineral oil) (0.58 g.), 1-chlorocarbonyl-4-methylpiperazine (0.5 g.) in anhydrous tetrahydrofuran (5 cc.) and hexamethylphosphotriamide (4.5 cc.), a product (1.3 g.), melting at 215° C., is obtained. After washing with diisopropyl ether (30 cc.), this product is dissolved in methylene chloride (40 cc.). After filtration, the solution is concentrated to dryness to yield 3-(4-methylpiperazin-1-yl)carbonyloxy-2-(1,6-naphthyridin-2-yl)isoindolin-1-one (1 g.) melting at 215° C.

2-(1,6-Naphthyridin-2-yl)-3-hydroxy-isoindolin-1-one can be prepared in the following way:
Preparation of 2-amino-1,6-naphthyridine, m.p. 239° C., according to E. M. Hawes and D. K. J. Gorecki, J. Med. Chem., 16, 849 (1973).
Preparation of 2-(1,6-naphthyridin-2-yl)phthalimide (2.7 g.), m.p. 265° C., from 2-amino-1,6-naphthyridine (1.45 g.) and phthalic anhydride (1.48 g.) in diphenyl ether (30 cc.) at 180° C. for 3 hours. Preparation of 2-(1,6-naphthyridin-2-yl)-3-hydroxy-isoindolin-1-one (1.5 g.), m.p. 239° C., from 2-(1,6-naphthyridin-2-yl)phthalimide (2.45 g.) in a mixture (24 cc.) of methanol and dioxan (50—50 by volume) and potassium borohydride (0.4 g.) at 24° C. for 4 hours.

EXAMPLE 8

1-Chlorocarbonyl-4-methylpiperazine (12 g.) is added to a suspension of 5-hydroxy-6-(5-methyl-1,8-naphthyridin-2-yl)-7-oxo-6,7-dihydro-5H-pyrrolo[3,4-b]-pyrazine (7.2 g.) in anhydrous pyridine (123 cc.). The reaction mixture is then heated at a temperature of about 50° C. for 2 hours. After cooling, the suspension obtained is poured into a mixture of water (750 cc.), a saturated aqueous solution of sodium bicarbonate (250 cc.) and methylene chloride (250 cc.). The aqueous layer is decanted and washed four times with methylene chloride (100 cc.). The organic layers are combined, washed four times with water (100 cc.), dried over anhydrous sodium sulphate, filtered and evaporated to dryness under reduced pressure. The residue obtained is dissolved in methylene chloride (50 cc.) and the resulting solution is filtered through silica gel (200 g.) in a column 3.8 cm. in diameter. Elution is carried out with pure methylene chloride (1,000 cc.) and then with a mixture (800 cc.) of methylene chloride and methanol (95-5 by volume). These eluates are discarded. Elution is then carried out with a mixture (1,200 cc.) of methylene chloride and methanol (95-5 by volume); the corresponding eluate is concentrated to dryness under reduced pressure. After recrystallisation of the residue from acetonitrile (40 cc.), 6-(5-methyl-1,8-naphthyridin-2-yl)-5-(4-methylpiperazin-1-yl)-carbonyloxy-7-oxo-6,7-dihydro-5H-pyrrolo[3,4-b]pyrazine (5.1 g.), which melts at 184° C., is obtained.

5-Hydroxy-6-(5-methyl-1,8-naphthyridin-2-yl)-7-oxo-6,7-dihydro-5H-pyrrolo[3,4-b]pyrazine, m.p. 260° C. with decomposition, can be prepared by reacting potassium borohydride with 6-(5-methyl-1,8-naphthyridin-2-yl)-5,7-dioxo-6,7-dihydro-5H-pyrrolo[3,4-b]pyrazine in a mixture of dioxan and water (97-3 by volume) at a temperature of about 20° C.

6-(5-Methyl-1,8-naphthyridin-2-yl)-5,7-dioxo-6,7-dihydro-5H-pyrrolo[3,4-b]pyrazine can be prepared by adding dicyclohexylcarbodiimide (258 g.) to a suspension of 3-(5-methyl-1,8-naphthyridin-2-yl)carbamoyl-pyrazine-2-carboxylic acid (77 g.) in anhydrous dimethylformamide (2,500 cc.). The reaction mixture is then stirred for 72 hours at a temperature of about 20° C. The dicyclohexylurea which has crystallised is then filtered off and washed with dimethylformamide (300 cc.) and diisopropyl ether (200 cc.). Diisopropyl ether (25 liters) is then added to the filtrate. The product which crystallises is filtered off and then washed with diisopropyl ether (2,000 cc.) to yield, after drying, 6-(5-methyl-1,8-naphthyridin-2-yl)-5,7-dioxo-6,7-dihydro-5H-pyrrolo[3,4-b]pyrazine (60.9 g.), which melts with decomposition at 265° C.

3-(5-Methyl-1,8-naphthyridin-2-yl)carbamoyl-pyrazine-2-carboxylic acid, m.p. 265° C. with decomposition, can be prepared by condensing pyrazine-2,3-dicarboxylic acid anhydride with 2-amino-5-methyl-1,8-naphthyridine in refluxing acetonitrile.

2-Amino-5-methyl-1,8-naphthyridine can be prepared according to the method described by E. V. Brown, J. Org. Chem. 30, 1607 (1965).

Pyrazine-2,3-dicarboxylic acid anhydride can be prepared according to the method described by S. Gabriel and A. Sonn, Chem. Ber., 40, 4850 (1907).

EXAMPLE 9

Sodium hydride (50% dispersion in mineral oil) (1.83 g.) is added all at once to a suspension of 7-hydroxy-6-(7-chloro-1,8-naphthyridin-2-yl)-5-oxopyrrolo[3,4-b]pyridine (5.4 g.) in anhydrous dimethylformamide (55 cc.). When the evolution of gas has ceased, a solution of 1-chlorocarbonyl-4-methylpiperazine (6.2 g.) in anhydrous dimethylformamide (62 cc.) is added over the course of 5 minutes. The reaction mixture is stirred for 2 hours at a temperature of about 20° C. and then anhydrous hexamethylphosphotriamide (70 cc.) is added. After standing for 18 hours, the reaction mixture is poured into ice-water (550 cc.). The precipitate which appears is filtered off, washed with water (4 cc.) and dried; a crude product (2.6 g.) is thus obtained. The aqueous filtrate is extracted three times with methylene chloride (100 cc.). The combined extracts are washed with water (150 cc.), dried over sodium sulphate and concentrated to a volume of 50 cc. Diisopropyl ether (110 cc.) is then added, and the product which crystallises is filtered off; a crude product (1.1 g.) is thus obtained.

All the crude product (3.7 g.) is dissolved in methylene chloride (90 cc.) and the solution obtained is passed through a column of silica gel (37 g.). Elution is first carried out with methylene chloride (6 × 90 cc.) and then with a mixture (3 × 40 cc.) of methylene chloride and methanol (50—50 by volume). The last three fractions are concentrated to dryness and a wet product (3.7 g.) is obtained which is recrystallised from the dimethyl ether of glycol (600 cc.). 6-(7-Chloro-1,8-naphthyridin-2-yl)-7-(4-methylpiperazin-1-yl)-carbonyloxy-5-oxo-pyrrolo[3,4-b]pyridine (1.85 g.), melting at 270° C., is thus obtained.

7-Hydroxy-6-(7-chloro-1,8-naphthyridin-2-yl)-5-oxo-pyrrolo[3,4-b]pyridine can be prepared in the following way:

Preparation of 2-(7-hydroxy-1,8-naphthyridin-2-yl)-quinolinimide (31.6 g.), m.p. 364° C., from 2-amino-7-hydroxy-1,8-naphthyridine (24.2 g.), quinolinic anhydride (45 g.) in acetic acid (120 cc.) and acetic anhydride (45 cc.) at 130°–135° C. for 1 hour.

Preparation of 2-(7-chloro-1,8-naphthyridin-2-yl)quinolinimide (11.4 g.), m.p. 278° C., from 2-(7-hydroxy-1,8-naphthyridin-2-yl)quinolinimide (14 g.) in phosphorus oxychloride (80 cc.) and dimethylformamide (2 cc.) for 1 hour at 95°–97° C.

Preparation of 6-(7-chloro-1,8-naphthyridin-2-yl)-7-hydroxy-5-oxo-pyrrolo[3,4-b]pyridine (7.1 g.), m.p. 290° C., from 2-(7-chloro-1,8-naphthyridin-2-yl)quinolinimide (10.4 g.) and potassium borohydride (1.36 g.) in a mixture (410 cc.) (50—50 by volume) of methanol and dioxan at 10°–15° C. for 30 minutes.

EXAMPLE 10

Following the procedure of Example 9 but starting with a suspension of 6-(7-methyl-1,8-naphthyridin-2-yl)-7-hydroxy-5-oxo-pyrrolo[3,4-b]pyridine (2.7 g.) in anhydrous tetrahydrofuran (27 cc.), sodium hydride (50% dispersion in mineral oil) (0.885 g.) and 1-chlorocarbonyl-4-methylpiperazine (3 g.) dissolved in anhydrous tetrahydrofuran (30 cc.), a reaction mixture is obtained which is poured into ice-water (210 cc.). The mixture is extracted with methylene chloride (3 × 400 cc.). The combined extracts are dried over potassium carbonate and are concentrated to dryness. A residue weighing 4.9 g. is thus obtained and is triturated with diisopropyl ether (60 cc.). The precipitate which appears is filtered off. The resulting product (3.6 g.) is dissolved in methylene chloride (72 cc.), and the solution is passed through a column of silica gel (36 g.). Elution is carried out successively with methylene chloride (3 × 500 cc.), a mixture (3 × 500 cc.) of methylene chloride and ethyl acetate (50—50 by volume), pure ethyl acetate (3 × 500 cc.) and a mixture (4 × 500 cc.) of ethyl acetate and methanol (90-10 by volume). The last four eluates are concentrated to dryness and the residue obtained is recrystallised from acetonitrile (58 cc.). 6-(7-Methyl-1,8-naphthyridin-2-yl)-7-(4-methylpiperazin-1-yl)-carbonyloxy-5-oxo-pyrrolo[3,4-b]pyridine (1.12 g.), melting at 226° C., is thus obtained.

6-(7-Methyl-1,8-naphthyridin-2-yl)-7-hydroxy-5-oxo-pyrrolo[3,4-b]pyridine can be prepared in the following way:
Preparation of 3-N-(7-methyl-1,8-naphthyridin-2-yl)carbamoyl-pyridine-2-carboxylic acid by heating 2-amino-7-methyl-1,8-naphthyridine (10.6 g.) and quinolinic anhydride (10.9 g.) in acetonitrile (200 cc.) under reflux for 15 minutes. A product (16.1 g.), which melts at 220° C., is thus obtained.
Preparation of (7-methyl-1,8naphthyridin-2-yl)quinolinimide by treating the aforesaid acid with acetyl chloride (2.8 cc.) in acetic acid (40 cc.). The mixture is kept at 85° C. for 30 minutes and is then cooled and filtered. A product (5.2 g.), melting at 270° C., is collected. Preparation of 6-(7-methyl-1,8-naphthyridin-2-yl)-7-hydroxy-5-oxo-pyrrolo[3,4-b]pyridine (2.7 g.), m.p. 260° C., from 2-(7-methyl-1,8-naphthyridin-2-yl)quinolinimide (3.7 g.) and sodium borohydride (0.69 g.) in methanol (38 cc.).

EXAMPLE 11

4-Methylpiperazine (8 g.) is added all at once to a suspension of 2-(1,8-naphthyridin-2-yl)-3-phenoxycarbonyloxy-isoindolin-1-one (5.6 g.) in acetonitrile (100 cc.). The solution obtained is stirred for 6 hours at a temperature of about 20° C. The reaction mixture is poured into a suspension of ice (100 g.) in methylene chloride (300 cc.). An 8% aqueous solution of sodium bicarbonate (200 cc.) is added to the suspension obtained. The organic phase is decanted and the aqueous phase is extracted with methylene chloride (400 cc.). The combined organic phases are dried over anhydrous potassium carbonate (10 g.) and concentrated to dryness. The oily residue (8 g.) is taken up in refluxing diisopropyl ether (100 cc.). On cooling the solution, crystals are deposited and are filtered off. 3-(4-Methyl-piperazin-1-yl)carbonyloxy-2-(1,8-naphthyridin-2-yl)isoindolin-1-one (2.9 g.), which melts at 183° C., is thus obtained.

2-(1,8-Naphthyridin-2-yl)-3-phenoxycarbonyloxy-isoindolin-1-one can be prepared in the following way: Preparation of 2-amino-1,8-naphthyridine, m.p. 141° C., according to W. W. Paudler and T. J. Kress, J. Org. Chem., 33, 1384 (1968). Preparation of 2-(1,8-naphthyridin-2-yl)phthalimide (8.6 g.), m.p. 250° C., by reacting 2-amino-1,8-naphthyridine (9.9 g.) with phthalic anhydride (10.2 g.) in dimethylformamide (75 cc.) at 150° C. for 1 hour 30 minutes. Preparation of 2-(1,8-naphthyridin-2-yl)-3-hydroxy-isoindolin-1-one (6.7 g.), m.p. 228° C., by reacting potassium borohydride (1.27 g.) with 2-(1,8-naphthyridin-2-yl)-phthalimide (8.6 g.) in dioxan (78 cc.) and a saturated aqueous solution of disodium phosphate (15.6 cc.) at 20° C. Preparation of 2-(1,8-naphthyridin-2-yl)-3-phenoxycarbonyloxy-isoindolin-1-one (5.6 g.), m.p. 110°–112° C., by reacting phenyl chloroformate (5.6 g.) with 2-(1,8-naphthyridin-2-yl)-3-hydroxy-isoindolin-1-one (3.9 g.) in anhydrous pyridine (70 cc.) at a temperature of about 20° C.

EXAMPLE 12

Following the procedure of Example 11 but starting with 2-(7-methyl-1,8-naphthyridin-2-yl)-3-phenoxycarbonyloxy-isoindolin-1-one (4.9 g.) and 4-methylpiperazine (6 g.) in acetonitrile (40 cc.) and stirring the reaction mixture for 24 hours at 25° C., a crude product (4.2 g.) is obtained. This product is triturated in diethyl ether (42 cc.) and then recrystallised from diisopropyl ether (300 cc.). 2-(7-Methyl-1,8-naphthyridin-2-yl)-3-(4-methylpiperazin-1-yl)carbonyloxy-isoindolin-1-one (1.1 g.), melting at 190° C., is thus obtained.

2-(7-Methyl-1,8-naphthyridin-2-yl)-3-phenoxycarbonyloxy-isoindolin-1-one can be prepared in the following way:
Preparation of 2-amino-7-methyl-1,8-naphthyridine, m.p. 186°–187° C., according to E. V. Brown, J. Org. Chem., 30, 1607 (1965).
Preparation of 2-(7-methyl-1,8-naphthyridin-2-yl)phthalimide (5.4 g.) by reacting 7-methyl-2-amino-1,8-naphthyridine (3.18 g.) with phthalic anhydride (2.96 g.) in diphenyl ether (60 cc.) for 1 hour at 170° C. Preparation of 2-(7-methyl-1,8-naphthyridin-2-yl)-3-hydroxy-isoindolin-1-one (5.8 g.), m.p. 208° C., by reacting potassium borohydride (0.9 g.) with 2-(7-methyl-1,8-naphthyridin-2-yl)phthalimide (6.2 g.) in a mixture (60 cc.) of methanol and dioxan (50—50 by volume).
Preparation of 2-(7-methyl-1,8-naphthyridin-2-yl)-3-phenoxycarbonyloxy-isoindolin-1-one (4.9 g.), m.p. 220° C. with decomposition, by reacting phenyl chloroformate (9.2 g.) with 2-(7-methyl-1,8-naphthyridin-2-yl)-3-hydroxy-isoindolin-1-one (5.8 g.) in anhydrous pyridine (160 cc.) at 5° C. for 15 minutes and then for 1 ½ hours at 25° C.

EXAMPLE 13

The procedure of Example 11 is followed but starting with 2-(7-chloro-1,8-naphthyridin-2-yl)-5-chloro-3-phenoxycarbonyloxy-isoindolin-1-one (1.25 g.) and 4-methylpiperazine (1.07 g.) in acetonitrile (33 cc.) and stirring for 24 hours at a temperature of about 20° C. From the reaction mixture, the resulting precipitate is filtered off and washed successively with acetonitrile (6 cc.) and diethyl ether (6 cc.). The product obtained (0.93 g.) is dissolved in methylene chloride (35 cc.), and the solution passed through a column of silica gel (10 g.). Elution is carried out with methylene chloride (16 × 20 cc.); the corresponding eluates are discarded. Elution is then carried out with ethyl acetate (5 × 20 cc.); the corresponding eluates are combined and concentrated under reduced pressure. A crystalline residue (0.9 g.) is obtained and is suspended in ethyl acetate (20 cc.). The crystals are filtered off and dried to yield 3-(4-methylpiperazin-1-yl)carbonyloxy-5-chloro-2-(7-chloro-1,8-naphthyridin-2-yl)isoindolin-1-one (0.75 g.) melting at 255° C.

2-(7-Chloro-1,8-naphthyridin-2-yl)-3-phenoxycarbonyloxy-5-chloro-isoindolin-1-one can be prepared in the following way:

Preparation of 4-chlorophthalic anhydride, m.p. 96° C., according to E. E. Ayling, J. Chem. Soc., 1929, 253. Preparation of 2-amino-7-hydroxy-1,8-naphthyridine, m.p. 300°–305° C., according to S. Carboni et al, Ann. Chim. (Roma), 54, 883 (1964).

Preparation of 2-(7-hydroxy-1,8-naphthyridin-2-yl)-5-chlorophthalimide (7 g.), m.p. 320° C., by reacting 2-amino-7-hydroxy-1,8-naphthyridine (9.5 g.) with 4-chlorophthalic anhydride (21.5 g.) in acetic acid (450 cc.) for 1 hour at 116° C. Preparation of 2-(7-chloro-1,8-naphthyridin-2-yl)-5-chlorophthalimide (6.4 g.), m.p. 280° C., by reacting phosphorus oxychloride (70 cc.) with 2-(7-hydroxy-1,8-naphthyridin-2-yl)-5-chlorophthalimide (7 g.) in the presence of dimethylformamide (0.7 cc.). By reacting potassium borohydride (0.75 g.) with 2-(7-chloro-1,8-naphthyridin-2-yl)-5-chlorophthalimide (6.4 g.) in a mixture (300 cc.) of dioxan and methanol(50-50 by volume), a mixture (5.2 g.) of 2-(7-chloro-1,8-naphthyridin-2-yl)-5-chloro-3-hydroxy-isoindolin-1-one and 2-(7-chloro-1,8-naphthyridin-2-yl)-6-chloro-3-hydroxy-isoindolin-1-one is obtained. This mixture is recrystallised firstly from dichloroethane (700 cc.) and then a second time from the same solvent (315 cc.). A product (1.51 g.) is thus obtained and is recrystallised successively from bromoform (38 cc.) and then from a mixture (104.5 cc.) of dichloroethane and ethanol (91-9 by volume). 2-(7-Chloro-1,8-naphthyridin-2-yl)-5-chloro-3-hydroxy-isoindolin-1-one (0.65 g.) is thus obtained. Preparation of 2-(7-chloro-1,8-naphthyridin-2-yl)-5-chloro-3-phenoxycarbonyloxy-isoindolin-1-one (1.6 g.), m.p. 220°–230° C., from 2-(7-chloro-1,8-naphthyridin-2-yl)-5-chloro-3-hydroxy-isoindolin-1-one (1 g.) and phenyl chloroformate (1.36 g.) in anhydrous pyridine (15 cc.).

EXAMPLE 14

The procedure of Example 11 is followed but starting with 2-(5-chloro-1,8-naphthyridin-2-yl)-3-phenoxycarbonyloxy-isoindolin-1-one (6.7 g.), 4-methylpiperazine (15.8 g.) and dimethylformamide (32 cc.) and stirring for 15 minutes at 23° C. The reaction mixture is then diluted by adding diisopropyl ether (320 cc.). The precipitate is filtered off, washed with diisopropyl ether (3 × 30 cc.) and then dried. A product (3.8 g.) is obtained which is recrystallised from acetonitrile (300 cc.) to yield 2-(5-chloro-1,8-naphthyridin-2yl)-3-(4-methylpiperazin-1-yl)carbonyloxy-isoindolin-1-one (2.9 g.) melting at 240° C.

2-(5-Chloro-1,8-naphthyridin-2-yl)-3-phenoxycarbonyloxy-isoindolin-1-one can be prepared in the following way:

Preparation of 2-amino-5-hydroxy-1,8-naphthyridine, m.p. 300°–305° C., according to S. Carboni et al, Gazz. Chim. Ital., 101, 136 (1971).

Preparation of 2-(5-hydroxy-1,8-naphthyridin-2-yl)-phthalimide (9.9 g.), m.p. 310° C., by reacting phthalic anhydride (17.8 g.) with 2-amino-5-hydroxy-1,8-naphthyridine (9.65 g.) in acetic acid (150 cc.) and acetic anhydride (30 cc.) at 124° C. for 2 hours.

Preparation of 2-(5-chloro-1,8-naphthyridin-2-yl)-phthalimide (6.1 g.), m.p. 280° C., by reacting phosphorus oxychloride (90 cc.) with 2-(5-hydroxy-1,8-naphthyridin-2-yl)phthalimide (9 g.) in the presence of dimethylformamide (3 cc.) for 1 hour at 107° C. Preparation of 2-(5-chloro-1,8-naphthyridin-2-yl)-3-hydroxy-isoindolin-1-one (5.1 g.), m.p. 260°–262° C., by reacting potassium borohydride (0.88 g.) with 2-(5-chloro-1,8-naphthyridin-2-yl)phthalimide (5.95 g.) in a mixture (65 cc.) of methanol and dioxan (50-50 by volume) at 21° C. for 24 hours. Preparation of 2-(5-chloro-1,8-naphthyridin-2-yl)-3-phenoxycarbonyloxy-isoindolin-1-one (6.7 g.), m.p. 212° C., by reacting phenyl chloroformate (7.4 g.) with 2-(5-chloro-1,8-naphthyridin-2-yl)-3-hydroxy-isoindolin-1-one (4.9 g.) in anhydrous pyridine (120 cc.) between 3° and 6° C. for 18 hours.

EXAMPLE 15

Anhydrous piperazine (5.15 g.) is added to a suspension of 2-(7-chloro-1,8-naphthyridin-2-yl)-3-phenoxycarbonyloxy-isoindolin-1-one (5.2 g.) in acetonitrile (32 cc.). The reaction mixture is stirred for 1 hour at a temperature of about 20° C. and diisopropyl ether (150 cc.) is then added. The insoluble product is filtered off and washed with a mixture (20 cc.) of acetonitrile and diisopropyl ether (50—50 by volume) and then with diisopropyl ether (50 cc.). After recrystallisation of the product thus obtained from a mixture (160 cc.) of acetonitrile and methanol (90—10 by volume), 2-(7-chloro-1,8-naphthyridin-2-yl)-3-(piperazin-1-yl)carbonyloxy-isoindolin-1-one (2.4 g.), melting with decomposition at 245° C., is obtained.

2-(7-Chloro-1,8-naphthyridin-2-yl)-3-phenoxycarbonyloxy-isoindolin-1-one can be prepared in the following way:

Phenyl chloroformate (126 g.) is added to a suspension of 2-(7-chloro-1,8-naphthyridin-2-yl)-3-hydroxy-isoindlin-1-one (86.5 g.) in pyridine (980 cc.), whilst keeping the temperature at about 25° C. The reaction mixture is then stirred for 3 hours at a temperature of about 20° C. and is thereafter poured into ice-water (9,000 cc.). The product which crystallises is filtered off and washed with water (6 × 500 cc.) and rhen with acetonitrile (3 × 200 cc.). After drying, 2-(7-chloro-1,8-naphthyridin-2-yl)-3-phenoxycarbonyloxyisoindolin-1-one (96.7 g.), which melts with decomposition at 235° C., is obtained.

2-(7-Chloro-1,8-naphthyridin-2-yl)-3-hydroxyisoindolin-1-one can be prepared as described in Example 1.

EXAMPLE 16

Following the procedure of Example 15 but starting with 2-(7-chloro-1,8-naphthyridin-2-yl)3-phenoxycarbonyloxy-isoindolin-1-one (3.45 g.) and 1-(2-hydroxyethyl)piperazine (5.2 g.) in acetonitrile (21 cc.), 2-(7-chloro-1,8-naphthyridin-2-yl)-3-[4-(2-hydroxyethyl)-piperazin-1-yl]carbonyloxy-isoindolin-1-one (2 g.) melting at 179°14 180° C., is obtained.

EXAMPLE 17

Following the procedure of Example 15 but starting with 2-(7-chloro-1,8-naphthyridin-2-yl)-3-phenoxycarbonyloxy-isoindolin-1-one (3.45 g.) and 1-allylpiperazine (5.05 g.) in acetonitrile (21 cc.), 3-(4-allylpiperazin-1-yl)carbonyloxy-2-(7-chloro-1,8-naphthyridin-2-yl)isoindolin-1-one (1.65 g.), melting at 186°–187° C., is obtained.

EXAMPLE 18

Following the procedure of Example 15 but starting with 2-(7-chloro-1,8-naphthyridin-2-yl)-3-phenoxycarbonyloxy-isoindolin-1-one (2.58 g.) and 1-ethylpiperazine (3.42 g.) in acetonitrile (16 cc.), 2-(7-chloro-1,8-naphthyridin-2-yl)-3-(4-ethylpiperazin-1-yl)-carbonyloxy-isoindolin-1-one (1.4 g.), melting at 195° C., is obtained.

EXAMPLE 19

Following the procedure of Example 15 but starting with 2-(7-chloro-1,8-naphthyridin-2yl)-3-phenoxycarbonyloxy-isoindolin-1-one (4.32 g.) and 1-proparglypiperazine (6.2 g.) in acetonitrile (27 cc.), 2-(7-chloro-1,8-naphthyridin-2-yl)-3-(4-proparglypiperazin-1-yl)carbonyloxy-isoindolin-1-one (2.05 g.), melting at 210° C., is obtained.

EXAMPLE 20

Following the procedure of Example 15 but starting with 2-(7-chloro-1,8-naphthyridin-2-yl)-3-phenoxycarbonyloxy-isoindolin-1-one (2.47 g.) and 1-isopropylpiperazine (3.66 g.) in acetonitrile (15 cc.), 2-(7-chloro-1,8-naphthyridin-2-yl)-3-(4-isopropyl-piperazin-1-yl)carbonyloxy-isoindolin-1-one (2.25 g.), melting at 203°–204° C., is obtained.

EXAMPLE 21

Following the procedure of Example 15 but starting with 2-(7-chloro-1,8-naphthyridin-2-yl)-3-phenoxycarbonyloxy-isoindolin-1-one (9.9 g.) and 1-phenylpiperazine (18.6 g.) in acetonitrile (75 cc.), 2-(7-chloro-1,8-naphthyridin-2-yl)-3-(4-phenylpiperazin-1-yl)carbonyloxy-isoindlin-1-one (1.8 g.), melting at 217° C., is obtained.

EXAMPLE 22

Following the procedure of Example 15 but starting with 2-(7-chloro-1,8-naphthyridin-2-yl)-3-phenoxycarbonyloxy-isoindolin-1-one (5.1 g.) and 1-t.-butylpiperazine (5 g.) in acetonitrile (31 cc.), 2-(7-chloro-1,8-naphthyridin-2-yl)-3-(4-t.-butylpiperazin-1-yl)carbonyloxy-isoindolin-1-one (3.3 g.), melting at 240° C., is obtained.

1-t.-Butylpiperazine can be prepared in the following way:

A solution (447 cc.) of sodium ethoxide in ethanol of concentration 1.34 moles per liter, followed by a solution (1,305 cc.) of ammonia in ethanol of concentration 4.6 moles per liter, are added to a suspension of N,N-bis(2-chloroethyl)-t.-butylamine hydrochloride (140.7 g.) in ethanol (750 cc.). The reaction mixture is then heated at a temperature of about 60° C. for 1 hour, whilst keeping the ammonia refluxing by means of a condenser containing solid carbon dioxide. The ammonia is then allowed to dissipate, and the reaction mixture is cooled to a temperature of about 20° C. under a stream of nitrogen. A solution (894 cc.) of sodium ethoxide in ethanol of concentration 1.34 moles per liter is then added. The sodium chloride which precipitates is filtered off and then washed with ethanol (150 cc.). The filtrate is concentrated to dryness under reduced pressure and the residue obtained is taken up in diethyl ether (300 cc.). The insoluble product is filtered off and washed with diethyl ether (60 cc.). The filtrate is concentrated to dryness and then distilled under reduced pressure. 1-t.-butylpiperazine (8.8 g.), which boils at 85°–86° C. under a pressure of 28 mm.Hg, is thus obtained.

N,N-bis(2-Chloroethyl)-t-butylamine hydrochloride can be prepared according to the method described by A. Katritsky, J. Chem. Soc. B, 556 (1966).

EXAMPLE 23

A 3.16N solution (6.7 cc.) of sodium methoxide in methanol is added to a suspension of 1-methylpiperazine-1-oxide dihydrochloride (2.0 g.) in anhydrous methanol (10 cc.). After stirring for 10 minutes at 25° C., the suspension is treated with decolourising charcoal (0.1 g.) and then filtered. The methanolic filtrate is evaporated under reduced pressure (20 mm.Hg) at 40° C. maximum. The oily residue (2.0 g.) is dissolved in anhydrous acetonitrile (50 cc.) and 2-(7-chloro-1,8-naphthyridin-2-yl)-3-phenoxycarbonyloxy-isoindolin-1-one (2.15 g.) is added. The reaction mixture is heated for 4 hours at 50° C. and then stirred for 48 hours at a temperature of about 25° C., filtered and concentrated under reduced pressure. The residue (3.8 g.) is dissolved in methylene chloride (50 cc.). The solution is passed through a column of Merck silica (0.02–0.05) (60 g.). Elution is carried out successively with methylene chloride (50 cc.), ethyl acetate (50 cc.), a mixture (50 cc.) of ethyl acetate and methanol (80–20 volume), a mixture (50 cc.) of ethyl acetate and methanol (50—50 by volume), and finally with the same mixture of solvents (100 cc.). This last fraction is evaporated under reduced pressure. The residue obtained (0.9 g., m.p. about 200° C.) is dissolved in acetonitrile (10 cc.) and distilled water (1 cc.), near the boiling point. After cooling to 2° C., the crystals which have appeared are filtered off, washed with ice-cold acetonitrile (0.5 cc.) and dried under reduced pressure (20 mm.Hg). 4- [2-(7-chloro-1,8-naphthyridin-2-yl)-3-oxo-isoindolin-1-yl]oxycarbonyl -1-methyl-piperazine-1-oxide dihydrate (0.62 g.), melting at about 200° C. (decomposition), is obtained.

1-Methylpiperazine-1-oxide dihydrochloride can be prepared in the following way: Preparation of t.-butyl (4-methylpiperazin-1-yl)carboxylate (as an oil; 15.0 g.) by reacting t.-butyl azidoformate (12.9 g.) with 1-methylpiperazine (9.5 g.) in water (30 cc.) and tetrahydrofuran (15 cc.), and gradually adding 5N sodium hydroxide solution (19 cc.) at a temperature of about 20° C. Preparation of 1-methyl-4-t.-butoxycarbonylpiperazine-1-oxide hydrochloride (8.7 g.), m.p. 233° C., by reacting 4-nitroperbenzoic acid (34.0 g.) with t.-butyl (4-methylpiperazin-1-yl)-carboxylate (24.2 g.) in anhydrous chloroform (240 cc.), at a temperature not exceeding 40° C. Preparation of 1-methylpiperazine-1-oxide dihydrochloride (5.5 g.) m.p. 205° C., by reacting anhydrous gaseous hydrogen chloride (2.35 g.) with 1-methyl-4-t.-butoxycarbonyl-piperazine-1-oxide hydrochloride (8.1 g.) in anhydrous ethanol (60 cc.), under reflux for 30 minutes.

EXAMPLE 24

1-Methylpiperazine (5.75 cc.) is added to a suspension of 6-(7-chloro-1,8-naphthyridin-2-yl)-7-oxo-5-phenoxycarbonyloxy-6,7-dihydro-5H-pyrrolo[3,4-b]-pyrazine (5 g.) in acetonitrile (31 cc.). The reaction mixture is stirred for 1 hour at a temperature of about 20° C. and diisopropyl ether (50 cc.) is then added. The ether (300 cc.) and the insoluble product is filtered off and washed with diisopropyl ether (40 cc.). After drying, a product (3.6 g.), which melts at about 185° C., is obtained and is dissolved in methylene chloride (150 cc.). The resulting solution is filtered over silica gel (95 g.) in a column 3.2 cm in diameter. Elution is carried out successively with methylene chloride (1,000 cc.), a mixture (500 cc.) of methylene chloride and ethyl acetate (72—25 by volume), a mixture (300 cc.) of methylene chloride and ethyl acetate (50—50 by volume) and pure ethyl acetate (1,500 cc.). These eluates are discarded. Elution is then carried out with a mixture (1,750 cc.) of ethyl acetate and methanol (90—10 by volume); the corresponding eluate is concentrated to dryness under reduced pressure. On recrystallising the residue from acetonitrile (38 cc.), 6-(7-chloro-1,8-naphthyridin-2-yl)-5-(4-methylpiperazin-1-yl)carbonyloxy-7-oxo-6,7-dihydro-5H-pyrrolo-[3,4-b]pyrazine (1.3 g.), melting at 245° C., is obtained.

6-(7-Chloro-1,6-naphthyridin-2-yl)-7-oxo-5-phenoxycarbonyloxy-6,7-dihydro-5H-pyrrolo[3,4-b]pyrazine can be prepared by adding phenyl chloroformate (9.4 g.) to a suspension of 6-(7-chloro-1,8-naphthyridin-2-yl)5-hydroxy-7-oxo-6,7-dihydro-5H-pyrrolo[3,4-b]pyrazine (6.3 g.) in anhydrous pyridine (63 cc.), with stirring and whilst keeping the temperature at about 5° C. When the addition is complete, the reaction mixture is gradually heated to 60° C. and this temperature is maintained for 1 hour. The reaction mixture is cooled and is then poured into distilled water (350 cc.) whilst keeping the temperature at about 10° C. The insoluble product is filtered off, and washed successively with water (120 cc.), acetonitrile (40 cc.) and diisopropyl ether (40 cc.). After drying, 6-(7-chloro-1,8-naphthyridin-2-yl)-7-oxo-5-phenoxycarbonyloxy-6,7-dihydro-5H-pyrrolo[3,4-b]pyrazine (7.2 g.), melting at 270° C., is obtained.

6-(7Chloro-1,8-naphthyridin-2-yl)-5-hydroxy-7-oxo-6,7-dihydro-5H-pyrrolo[3,4,-b]pyrazine can be prepared by adding potassium borohydride (0.97 g.) to a suspension of 6-(7-chloro-1,8-naphthyridin-2-yl)-5,7-dioxo-6,7-dihydro-5H-pyrrolo[3,4-b]pyrazine (7.45 g.) in a mixture (288 cc.) of dioxan and methanol (50—50 by volume), with stirring and whilst keeping the temperature at about 3° C. After stirring for 2 hours at a temperature of about 3° C., the insoluble product is filtered off and washed successively with a mixture (24 cc.) of dioxan and methanol (50—50 by volume), water (24 cc.), a mixture (24 cc.) of dioxan and methanol (50—50 by volume) and diisopropyl ether (12 cc.). After drying, 6-(7-chloro-1,8-naphthyridin-2-yl)-5-hydroxy-7-oxo-6,7-dihydro-5H-pyrrolo[3,4-b]-pyrazine (5.3 g.), melting wit decomposition at 270° C., is obtained.

6-(7-Chloro-1,8-naphthyridin-2-yl)-5,7-dioxo-6,7-dihydro-5H-pyrrolo[3,4-b]pyrazine can be prepared by adding 6-(7-hydroxy-1,8-naphthyridin-2-yl)-5,7-dioxo-6,7-dihydro-5H-pyrrolo[3,4-b]pyrazine (32 g.) gradually, and at a temperature of about 15° C., to a solution of dimethylformamide (3.8 cc.) in phosphorus oxychloride (128 cc.). When the addition is complete, the reaction mixture is heated under reflux for half an hour and is the cooled and poured in small portions into crushed ice (1.3 kg.). The insoluble product is filtered off and then washed with water until the wash liquors are at pH 5. After drying, 6-(7-chloro-1,8-naphthyridin-2-yl)-5,7-dioxo-6,7-dihydro5H-pyrrolo[3,4-b]pyrazine (21.3 g.), melting with decomposition at about 340° C., is obtained.

6-(7-Hydroxy-1,8-naphthyridin-2-yl)-5,7-dioxo-6,7-dihydro-5H-pyrrolo[3,4-b]pyrazine can be prepared by heating under reflux a suspension of 2-amino-7-hydroxy-1,8-naphthyridine (22.4 g.) and pyrazine-2,3,-dicarboxylic acid anhydride (23 g.) in acetic acid (280 cc.). After refluxing for 1 hour, the reaction mixture is cooled to a temperature of about 30° C, and acetic anhydride (280 cc.) is added. The reaction mixture is again heated under reflux for 10 minutes and is then cooled to a temperature of about 20° C. The insoluble product is fltered off and then washed with acetic acid (40 cc.) and diisopropyl ether (200 cc.). After drying, 6-(7-hydroxy-1,8-naphthyridin-2-yl)-5,7-dioxo-6,7-dihydro-5H-pyrrolo[3,4-b]-pyrazine (32.1 g.), melting at 373° C., is obtained.

2-Amino-7-hydroxy-1,8-naphthyridine can be prepared according to the method described by S. Carboni et al, Gazz. Chim. Ital., 95, 1498 (1965).

EXAMPLE 25

1-Methylpiperazine (8.15 g.) is added to a suspension of 6-(7-methoxy-1,8-naphthyridin-2-yl)-7-oxo-5-phenoxycarbonyloxy-6,7-dihydro-5H-pyrrolo[3,4-b]-pyrazine (5 g.) in dimethylformamide (50 cc.). The reaction mixture is stirred for 7 minutes at a temperature of about 17° C. and diisopropyl ether (250 cc.) is then added. The insoluble product is filtered off, washed with diisopropyl ether (30 cc.) and dried. The product obtained is dissolved in methylene chloride (130 cc.), and the solution chromatographed on silica gel (90 g.) in a column 2.4 cm. in diameter. Elution is carried out successively with a mixture (130 cc.) of methylene chloride and ethyl acetate (75—25 by volume), a mixture (130 cc.) of methylene chloride and ethyl acetate (50—50 by volume), a mixture (130 cc.) of methylene chloride and ethyl acetate (25—75 by volume), pure ethyl acetate (780 cc.), a mixture (390 cc.) of ethyl acetate and methanol (98—2 by volume), a mixture (390 cc.) of ethyl acetate and methanol (96—4 by volume) and a mixture (650 cc.) of ethyl acetate and methanol (90—10 by volume). These eluates are discarded. Elution is then carried out with a mixture (1,300 cc.) of ethyl acetate and methanol (90—10 by volume). The corresponding eluate is concentrated to dryness under reduced pressure. After recrystallising the residue from acetonitrile (62 cc.), 6-(7-methoxy-1,8-naphthyridin-2-yl)-5-(4-methylpiperazin-1-yl)carbonyloxy-7-oxo-6,7-dihydro-5H-pyrrolo[3,4-b]pyrazine (1.8 g.), melting at 237° C., is obtained.

6-(7-Methoxy-1,8-naphthyridin-2-yl)-7-oxo-5-phenoxycarbonyloxy-6,7-dihydro-5H-pyrrolo[3,4-b]pyrazine, m.p. 255° C., can be prepared by reacting phenyl chloroformate with 5-hydroxy-6-(7-methoxy-1,8-naphthyridin-2-yl)-7-oxo-6,7-dihydro-5H-pyrrolo[3,4-b]pyrazine in anhydrous pyridine at a temperature of about 20° C.

5-Hydroxy-6-(7-methoxy-1,8-naphthyridin-2-yl)-7-oxo-6,7-dihydro-5H-pyrrolo-[3,4-b]pyrazine, m.p. 255° C., can be prepared by reacting potassium borohydride with 6-(7-methoxy-1,8-naphthyridin-2-yl)-5,7-dioxo-6,7-dihydro-5H-pyrrolo[3,4-b]pyrazine in a mixture of dioxan and water (98—2 by volume) at a temperature of about 20° C.

6-(7-Methoxy-1,8-naphthyridin-2-yl)-5,7-dioxo-6,7-dihydro-5H-pyrrolo[3,4-b]pyrazine, m.p. 296° C., can be prepared by reacting pyrazine-2,3-dicarboxylic acid anhydride with 2-amino-7-methoxy-1,8-napthyridine in acetic acid in the presence of acetic anhydride at the reflux temperature.

EXAMPLE 26

Following the procedure of Example 25 but starting with 6-(5,7-dimethyl-1,8-naphthyridin-2-yl)-7-oxo-5-phenoxycarbonyloxy-6,7-dihydro-5H-pyrrolo[3,4-b]pyrazine (2.8 g.) and 1-methylpiperazine (7 cc.) in dimethylformamide (7 cc.), 6-(5,7-dimethyl-1,8naphthyridin-2-yl)-5-(4-methylpiperazin-1-yl)carbonyloxy-7-oxo-6,7-dihydro-5H-pyrrolo[3,4-b]pyrazine (0.7 g.), melting at 255° C., is obtained.

6-(5,7-Dimethyl-1,8-naphthyridin-2-yl)-7-oxo-5-phenoxycarbonyloxy-6,7-dihydro-5H-pyrrolo[3,4-b]pyrazine, m.p. 220° C., can be prepared by reacting phenyl chlororformate with 6-(5,7-dimethyl-1,8-naphthyridin-2-yl)-5-hydroxy-7-oxo-6,7-dihydro-5H-pyrrolo[3,4-b]pyrazine in anhydrous pyridine at a temperature of about 2° C.

6-(5,7-Dimethyl-1,8-naphthyridin-2-yl)-5-hydroxy-7-oxo-6,7-dihydro-5H-pyrrolo[3,4-b]pyrazine, m.p. 265° C. with decomposition, can be prepared by reacting potassium borohydride with 6-(5,7-dimethyl-1,8-naphthyridin-2-yl)-5,7-dioxo-6,7-dihydro-5H-pyrrolo[3,4-b]pyrazine in a mixture of dioxan and water (99-1 by volume) at a temperature of about 20° C.

6-(5,7-Dimethyl-1,8-naphthyridin-2-yl)-5,7-dioxo-6,7-dihydro-5H-pyrrolo[3,4-b]pyrazine can be prepared by heating under reflux a suspension of 3-(5,7-dimethyl-1,8-naphthyridin-2-yl)carbamoyl-pyrazine-2-carboxylic acid (12 g.) in thionyl chloride (120 cc.). When the evolution of gas has ceased, the reaction mixture is cooled to a temperature of about 5° C. and diisopropyl ether (200 cc.) is then added. The insoluble product is filtered off and washed with diisopropyl ether (60 cc.). After drying, 6-(5,7-dimethyl-1,8-naphthyridin-2-yl)-5,7-dioxo-6,7-dihydro-5H-pyrrolo[3,4-b]pyrazine (11.5 g.), melting at about 250° C. with decomposition, is obtained.

3-(5,7-Dimethyl-1,8-naphthyridin-2-yl)carbamoyl-pyrazine-2-carboxylic acid, m.p. 255° C. with decomposition, can be prepared by reacting pyrazine-2,3-dicarboxylic acid anhydride with 2-amino-5,7-dimethyl-1,8-naphthyridine in anhydrous dimethylformamide at a temperature of about 100° C. 2-Amino-5,7-dimethyl-1,8-naphthyridine, which melts at 225°–226° C., can be prepared according to the method of J. Bernstein et al, J. Amer. Chem. Soc., 69, 1151 (1947).

EXAMPLE 27

A solution of 3-chloroperbenzoic acid (1.77 g.) in chloroform (60 cc.) is added to a solution of 6-(7-chloro-1,8-naphthyridin-2-yl)-5-(4-methylpiperazin-1-yl)carbonyloxy-7-oxo-6,7-dihydro-5H-pyrrolo[3,4-b]pyrazine (2.7 g.) in chloroform (45 cc.). The reaction mixture is stirred for 1 hour at a temperature of about 20° C. and a saturated aqueous solution of sodium bicarbonate (40 cc.) and methylene chloride (50 cc.) are then added. The aqueous layer is decanted and then washed twice with methylene chloride (50 cc.). The organic layers are combined, washed twice with water (30 cc.), dried over anhydrous sodium sulphate and then concentrated to dryness under reduced pressure. The residue is dissolved in methylene chloride (50 cc.) and the resulting solution is filtered through silica gel (25 g.) in a column 1.8 cm. in diameter. Elution is carried out successively with a mixture (620 cc.) of methylene chloride and methanol (94–6 by volume) and a mixture (190 cc.) of methylene chloride and methanol (90–10 by volume). These eluates are discarded. Elution is then carried out successively with a mixture (140 cc.) of methylene chloride and methanol (90–10 by volume), a mixture (330 cc.) of methylene chloride and methanol (85–15 by volume) and a mixture (330 cc.) of methylene chloride and methanol (80–20 by volume); the corresponding eluates are combined and concentrated to dryness under reduced pressure. After recrystallising the residue thus obtained from methanol (20 cc.), 4- 5-[6-(7-chloro-1,8-naphthyridin-2-yl)-7-oxo-6,7-dihydro-5H-pyrrolo[3,4-b]pyrazinyl]oxycarbonyl -1-methylpiperazine-1-oxide (0.6 g.), melting with decomposition at 245° C., is obtained.

EXAMPLE 28

Triethylamine (3.4 cc. equivalent to 2.44 g.), followed by pyridine (15 cc.) are added to a suspension of 2-(7-chloro-1,8-naphthyridin-2-yl)-5-fluoro-3-hydroxy-1-isoindolinone (2 g.) and 4-chlorocarbonyl-1-methyl-piperazine hydrochloride (3.6 g.) in methylene chloride (30 cc.). The suspension obtained is heated to the reflux temperature (55° C) for 1 hour and further 4-chlorocarbonyl-1-methylpiperazine (3.6 g.) and triethylamine (3.4 cc.) are then added. The mixture is further heated to the reflux temperature for 45 minutes. After cooling, methylene chloride (30 cc.) and water (60 cc.) are added. After phase separation, the aqueous layer is extracted with methylene chloride (60 cc.). The organic extracts are dried over anhydrous sodium sulphate. After filtration and concentration, the residue is triturated in water (30 cc.). The precipitate is filtered off and dried in air. The crude product is recrystallised from acetonitrile (64 cc.). The product is filtered off and then washed with isopropyl ether (60 cc.). This gives 2-(7-chloro-1,8-naphthyridin-2-yl)-5-fluoro-3-(4-methylpiperazinyl)-carbonyloxy-1-isoindolinone (0.8 g.) melting at 247°–248° C.

2-(7-chloro-1,8-naphthyridin-2-yl)-5-fluoro-3-hydroxy-1-isoindolinone can be prepared in the following manner:

2-diacetoxymethyl-4-fluoro-N-(7-chloro-1,8-naphthyridin-2-yl)-benzamide (6 g.) are added to a solution of sulphuric acid (d = 1.83) (12 cc.) in water (48 cc.). The mixture is heated to the reflux temperature for 15 minutes. After cooling, the precipitate is filtered off, washed with water (60 cc.) and then dried to constant weight. This gives 2-(7-chloro-1,8-naphthyridin-2-yl)-5-fluoro-3-hydroxy-1-isoindolinone (2 g.) melting at 245°–250° C.

2-Diacetoxymethyl-4-fluoro-N-(7-chloro-1,8-naphthyridin-2-yl)-benzamide can be prepared in the following manner:

Sulphuric acid (d = 1.83) (16.4 cc.) is added to a suspension of 4-fluoro-2-methyl-N-(7-chloro-1,8-naphthyridin-2-yl)-benzamide (10.3 g.) in acetic anhydride (120 cc.) cooled externally by means of an ice bath, the temperature being maintained below 10° C. After cooling to 2° C by means of a mixture of ethanol and solid carbon dioxide, chromic anhydride (8.9 g.) is added whilst maintaining the temperature at 2° C. The reaction mixture is stirred for a further 1 hour 30 minutes at 2° C and is then poured into iced water (700 g.). The precipitate formed is filtered off and then washed with iced water (450 cc.). After drying, 2-diacetoxymethyl- 4-fluoro-N-(7-chloro-1,8-maphthyridin-2-yl)-benzamide (6.4 g.) melting at about 182°–185° C is obtained.

4-Fluoro-2-methyl-N-(7-chloro-1,8-naphthyridin-2-yl)-benzamide can be prepared in the following manner: a solution of 2-amino-7-chloro-1,8-naphthyridine (7.5 g.) in acetonitrile (72 cc.) and pyridine (18 cc.) is added over the course of 20 minutes, at a temperature of 24°–36° C, to 4-fluoro-2-methyl-benzoyl chloride (7.2 g.). The precipitate formed during the reaction is filtered off, washed with acetonitrile (15 cc.) and then recrystallised from acetonitrile (280 cc.).

The mother liquors from the reaction are concentrated. After dissolving in methylene chloride (500 cc.) and washing with an 8% strength sodium bicarbonate solution (100 cc.), a second crop is obtained, which is recrystallised from acetonitrile (80 cc.). This gives 4-fluoro-2-methyl-N-(7-chloro-1,8-naphthyridin-2-yl)-benzamide (a total of 9.5 g.) melting at 145°–150° C.

4-Fluoro-2-methyl-benzoyl chloride is obtained by reaction of thionyl chloride at the reflux temperature with 4-fluoro-2-methyl-benzoic acid, which can in turn be prepared according to BUU-HOI and XUONG, J. Chem. Soc. p. 386 (1953).

EXAMPLE 29

On following the procedure of Example 28, but starting from 2-(7-chloro-1,8-naphthyridin-2-yl)-3-hydroxy-5-nitro-1-isoindolinone (5 g.) and 4-chlorocarbonyl-1-methyl-piperazine hydrochloride (12.2 g.) in methylene chloride (460 cc.) in the presence of triethylamine (9.5 cc.) and pyridine (46 cc.), a crude product (5.1 g.) is obtained, which is chromatographed on a column containing silica (0.2 14 0.05 mm) (100 g.). The column is eluted with chloroform, fractions of 100 cc. being collected.

Fractions 1 to 7 (700 cc.) are discarded and fractions 8 to 26 (1,900 cc.) after concentration yield a product (1.8 g.) which is recrystallised from a mixture of ethanol and acetonitrile (1/9 by volume). This gives 2-(7-chloro-1,8-naphthyridin-2-yl)-3-(4-methyl-piperazinyl)-carbonyloxy-5-nitro-1-isoindolinone (1.1 g.) melting at 250° C.

2-(7-Chloro-1,8-Naphthyridin-2-yl)-3-hydroxy-5-nitro-1-isoindolinone can be prepared in the following manner:

Sulphuric acid (d = 1.83) (25 cc.) is added to a suspension of 2-diacetoxymethyl-4-nitro-N-(7-chloro-1,8-naphthyridin-2-yl)-benzamide (17.6 g.) in ethanol (160 cc.) and water (120 cc.). The temperature rises from 26° to 45° C. Thereafter the mixture is heated to the reflux temperature for 15 minutes. After cooling, the precipitate obtained is filtered off, washed with water (250 cc.) and then dried. This gives 2-(7-chloro-1,8-naphthyridin-2-yl)-3-hydroxy-5-nitro-1-isoindolinone (8.8 g.) melting at a temperature above 300° C.

2-Diacetoxymethyl-4-nitro-N-(7-chloro-1,8-naphthyridin-2-yl)-benzamide can be prepared in the following manner:

Sulphuric acid (d = 1.83) (45 cc.) is added to a suspension of 2-methyl-4-nitro-N-(7-chloro-1,8-naphthyridin-2-yl)-benzamide (27.8 g.) in acetic anhydride (300 cc.), without exceeding 10° C, and thereafter chromic anhydride (2.43 g.) is added whilst maintaining the temperature at between −2° C and +1° C. The mixture is stirred for a further hour at 0° C and is then poured into iced water (2 liters). The precipitate is filtered off and washed with water (800 cc.). It is then treated with chloroform (1,500 cc.). The chloroform extracts are concentrated. This gives 2-diacetoxymethyl-4-nitro-N-(7-chloro-1,8-naphthyridin-2-yl)-benzamide (17.6 g.) melting at 230° C.

2-Methyl-4-nitro-N-(7-chloro-1,8-naphthyridin-2-yl)-benzamide can be prepared in the following manner:

2-Methyl-4-nitro-benzoyl chloride (16.1 g.) is added all at once to a suspension of 2-amino-7-chloro-1,8-naphthyridine (14.5 g.) in pyridine (161 cc.). The temperature rises to 40° C. The mixture is stirred for a further hour and water (640 cc.) is then added. The precipitate is filtered off and washed with water (225 cc.) and then with acetone (150 cc.). After recrystallisation from acetonitrile (1,600 cc.), 2-methyl-4-nitro-N-(7-chloro-1,8-naphthyridin-2-yl)-benzamide (26 g.) melting at 229° C is obtained.

2-Methyl-4-nitro-benzoyl chloride can be obtained according to the method described by YUNG, VOHRA and CHU, J. Pharm. Sc., 59, 1405 (1970).

EXAMPLE 30

On following the procedure of Example 28 but starting from 2-(7-chloro-1,8-naphthyridin-2-yl)-3-hydroxy-5-methoxy-1-isoindolinone (2.6 g.), 4-chlorocarbonyl-1-methylpiperazine hydrochloride (4.55 g.), triethylamine (4.7 cc., equivalent to 3.4 g.), pyridine (20 cc.) and methylene chloride (40 cc.), a product (3.6 g.) is obtained, which is chromatographed on silica (0.005 – 0.2 mm) (36 g.). The column is eluted with methylene chloride (2,000 cc.) and then with ethyl acetate (500 cc.), fractions of 100 cc. being collected.

After concentrating the various fractions, the product obtained is recrystallised from a mixture of ethanol and acetonitrile (50–50 by volume) (27 cc.). This gives 2-(7-chloro-1,8-naphthyridin-2-yl)-5-methoxy-3-(4-methylpiperazinyl)-carbonyloxy-1-isoindolinone (1 g.) melting at 206° C.

2-(7-Chloro-1,8-Naphthyridin-2-yl)-3-hydroxy-5-methoxy-1-isoindolinone can be prepared in the following manner:

A suspension of 4-methoxy-2-methyl-N-(7-chloro-1,8-naphthyridin-2-yl)-benzamide (3.3 g.), N-bromosuccinimide (4.45 g.) and azo-bis-isobutyronitrile (0.1 g.) in carbon tetrachloride (350 cc.) is heated to the reflux temperature for 20 hours. After cooling, the precipitate is filtered off. The filtrate is concentrated to dryness. The residue from the concentration is taken up in methylene chloride (24 cc.). The methylene chloride solution is filtered. The precipitate which has been isolated is suspended in an 8% strength sodium bicarbonate solution (10 cc.). It is stirred for 30 minutes. The precipitate is filtered off and then washed with water (6 cc.). This gives 2-(7-chloro-1,8-naphthyridin-2-yl)-3-hydroxy-5-methoxy-1-isoindolinone (0.4 g.) melting at 215°–220° C.

4-Methoxy-2-methyl-N-(7-chloro-1,8-naphthyridin-2-yl)-benzamide can be prepared in the following manner:

4-Methoxy-2-methyl-benzoyl chloride (33 g.) in pyridine (330 cc.) are added, at a temperture of about 20° C, to 2-amino-7-chloro-1,8-naphthyridine (32 g.). The reaction mixture is stirred for a further 3 hours and is then poured into water (2,700 cc.). The precipitate formed is filtered off and washed with water (300 cc.) and then with ethanol (200 cc.). After recrystallisation from ethanol (1,000 cc.), 4-methoxy-2-methyl-N-(7- chloro-1,8-naphthyridin-2-yl)-benzamide (25.5 g.) melting at 190° C are obtained.

4-Methoxy-2-methyl-benzoyl chloride (boiling point/0.3 mm Hg = 88° C) can be prepared by reaction of thionyl chloride at the reflux temperature with 4-methoxy-2-methylbenzoic acid.

4-Methoxy-2-benzoic acid can be prepared according to D. PELTIER, Bull. Soc. Chim. Bretagne, 31, 7 (1956) [Chem. Abstr. 52, 9017 (1958)].

EXAMPLE 31

On following the procedure of Example 28 but starting from 2-(7-chloro-1,8-naphthyridin-2-yl)-3-hydroxy-6-nitro-1-isoindolinone (7.12 g.) and 4-chlorocarbonyl-1-methylpiperazine hydrochloride (15.9 g.) in methylene chloride (250 cc.), pyridine (100 cc.) and triethylamine (12.4 cc.), a crude product (3.6 g.) is obtained, which is recrystallised from acetonitrile (25 cc.). This gives 2-(7-chloro-1,8-naphthyridin-2-yl)-3-(4-methyl-piperazinyl)-carbonyloxy-6-nitro-1-isoindolinone (1.1 g.), melting at 244° C.

2-(7-Chloro-1,8-naphthyridin-2-yl)-3-hydroxy-6-nitro-1-isoindolinone can be prepared in the following manner:

2-(7-Chloro-1,8-naphthyridin-2-yl)-3-hydroxy-1-isoindolinone (62.4 g.) is dissolved in sulphuric acid (d = 1.83) (600 cc.). The solution obtained is heated to 65° C and potassium nitrate (20.2 g.) is then added over the course of 2 minutes. The temperature is kept at 65°-70° C for a further 6 minutes. Thereafter the reaction mixture is poured onto ice (5 kg.). The mixture is stirred for 1 hour. The precipitate is filtered off, and is washed with water (3,000 cc.), an 8% strength sodium bicarbonate solution (1,000 cc.) and finally water (4,000 cc.). After recrystallisation from dimethylformamide (500 cc.), 2-(7-chloro-1,8-naphthyridin-2-yl)-3-hydroxy-6-nitro-1-isoindolinone (32 g.), melting at a temperature above 300° C, is obtained.

EXAMPLE 32

The procedure followed is as in Example 28, but using 4-chloro-2-(7-chloro-1,8-naphthyridin-2-yl)-3-hydroxy-1-isoindolinone (2 g.), 4-chlorocarbonyl-1-methyl-piperazine hydrochloride (6.9 g.), triethylamine (6.5 cc., equivalent to 4.7 g.), pyridine (30 cc.) and methylene chloride (200 cc.). When the reaction has ended, the reaction mixture is taken up in water (200 cc.). A precipitate which forms is filtered off. After decanting from the methylene chloride layer, the aqueous layer is extracted with methylene chloride (400 cc.). The combined organic layers are dried over anhydrous sodium sulphate (10 g.). After filtration followed by concentration, the residue is washed with water. The mother liquor is extracted with methylene chloride (100 cc.). After evaporation of the methylene chloride, the residue is chromatographed on silica gel (125 g.), elution being carried out with a mixture of methylene chloride and ethyl acetate (9/1 by volume), and fractions of 50 cc. being collected. Fractions 1 to 21 (1,050 cc.) yield isoindolinone starting material (0.9 g.) and fractions 22 to 25 (200 cc.) yield a product (0.3 g.) which is recrystallised from acetonitrile (6 cc.). This gives 4-chloro-2-(7-chloro-1,8-naphthyridin-2-yl)-3-(4-methyl-piperazinyl)-carbonyloxy-1-isoindolinone (0.2 g.), melting at 191°-193° C.

4-Chloro-2-(7-chloro-1,8-naphthyridin-2-yl)-3-hydroxy-1-isoindolinone can be prepared in the following manner:

Potassium borohydride (3 g.) is added to 4-chloro-N-(7-chloro-1,8-naphthyridin-2-yl)-phthalimide (25.2 g.) in dioxane (500 cc.) and methanol (500 cc.). The mixture is stirred for 4 hours at a temperature of about 20° C and water (500 cc.) is then added. The precipitate is filtered off and washed with water (100 cc.) and then with a mixture (200 cc.) of equal parts of methanol and dioxane. This gives a crude product (20 g.) which is chromatographed on silica (0.05 – 0.2 mm) (6 kg.) as indicated below, the eluate being collected in fractions of 5,000 cc. Elution is carried out first with methylene chloride (10,000 cc.) and then with a mixture of methylene chloride and ethyl acetate (5/5 by volume) (40,000 cc.). This eluate, after concentration, yields (4-chloro-2-(7-chloro-1,8-naphthyridin-2-yl)-3-hydroxy-1-isoindolinone (6 g.) melting at 270° C. Thereafter elution is carried out with the same mixture of methylene chloride and ethyl acetate (10,000 cc.). This eluate, after concentration, gives a mixture (1.6 g.) of the isomers 4-chloro-2-(7-chloro-1,8-naphthyridin-2-yl)-3-hydroxy-1-isoindolinone and 7-chloro-2-(7-chloro-1,8-naphthyridin-2-yl)-3-hydroxy-1-isoindolinone. Finally, elution is carried out again with the same mixture of methylene chloride and ethyl acetate (20,000 cc.). This eluate, after concentration, yields 7-chloro-2-(7-chloro-1,8-naphthyridin-2-yl)-3-hydroxy-1-isoindolinone (3.1 g.) melting at a temperature above 280° C.

4-Chloro-N-(7-chloro-1,8-naphthyridin-2-yl)-phthalimide can be obtained in the following manner:

3-Chlorophthalic anhydride (15 g.) and N-hydroxysuccinimide (11.8 g.) in dimethylformamide (375 cc.) are heated for 18 hours at 75°-80° C, 2-amino-7-chloro-1,8-naphthyridine (14.7 g.) and N,N'-dicyclohexylcarbodiimide (34 g.) are then added and the mixture is heated for a further 3 hours at 75°-80° C. After cooling, the precipitate is filtered off and washed with dimethylformamide (45 cc.) and ethanol (45 cc.). The precipitate obtained is exhaustively extracted with boiling ethanol (750 cc.). The product insoluble in ethanol is filtered off, thus giving 4-chloro-N-(7-chloro-1,8-naphthyridin-2-yl)-phthalimide (25.2 g.) melting at a temperature above 280° C.

3-Chlorophthalic anhydride can be prepared according to NEUMAN et al. J. Amer. Chem. Soc., 76, 5004 (1950).

EXAMPLE 33

On the following the procedure of Example 28 but starting from 7-chloro-2-(7-chloro-1,8-naphthyridin-2-yl)-3-hydroxy-1-isoindolinone (3 g.), 4-chlorocarbonyl-1-methyl-piperazine hydrochloride (10.3 g.), triethylamine (9.7 cc., equivalent to 7 g.) and pyridine (45 cc.) in methylene chloride (300 cc.), a crude product (3.6 g.) is obtained, which is chromatographed on silica (0.05 – 0.2 mm) (70 g.). Elution is first carried out with a mixture of methylene chloride and ethyl acetate (90/10 by volume) (2,600 cc.) and then with a mixture of ethyl acetate and methanol (90/10 by volume) (2,000 cc.), the eluate being collected in fractions of 200 cc.

This latter eluate (fractions 14 to 23) is concentrated to dryness and the residue (2.9 g.) is recrystallised from acetonitrile (90 cc.). This gives 7-chloro-2-(7-chloro-1,8-naphthyridin-2-yl)-3-(4-methyl-piperazinyl)-carbonyloxy-1-isoindolinone (2.3 g.) melting at 220° C.

7-Chloro-2-(7-chloro-1,8-naphthyridin-2-yl)-3-hydroxy-1-isoindolinone is obtained according to the process described in Example 32.

EXAMPLE 34

On following the procedure of Example 28, but starting from 6-bromo-2-(7-chloro-1,8-naphthyridin-2-yl)-3-hydroxy-1-isoindolinone (6 g.), 1-chlorocarbonyl-4-methyl-piperazine hydrochloride (18.4 g.), triethylamine (17.2 cc., equivalent to 12.4 g.) and pyridine (90 cc.) in methylene chloride (600 cc.), a crude product (6 g.) is obtained, which is chromatographed on silica (0.05 – 0.2 mm) (120 g.). Elution is carried out successively with a mixture of methylene chloride and ethyl acetate (70/30 by volume) (600 cc.), ethyl acetate (900 cc.) and again ethyl acetate (2,500 cc.), eluate fractions of 100 cc. being collected.

Fractions 16 to 40 are concentrated to dryness. This gives a product (5 g.) which is dissolved in methylene chloride (120 cc.). The solution is decolorised by means of animal charcoal (1 g.) and then filtered. Isopropyl ether (240 cc.) is added. The precipitate formed is filtered off and then dried. This gives 6-bromo-2-(7-chloro-1,8-naphthyridin-2-yl)-3-(4-methyl-piperazinyl)-carbonyloxy-1-isoindolinone (3.5 g.) melting at 258°–260° C.

6-Bromo-2-(7-chloro-1,8-naphthyridin-2-yl)-3-hydroxy-1-isoindolinone can be prepared in the following manner:

A solution of sodium nitrite (2.45 g.) in water (25 cc.) is added over the course of 35 minutes to a suspension of 6-amino-2-(7-chloro-1,8-naphthyridin-2-yl)-3-hydroxy-1-isoindolinone (10.5 g.) in 48% strength (by weight) aqueous hydrobromic acid (250 cc.) and water (50 cc.) cooled to 4° C. The mixture is stirred for a further hour whilst cooling it externally with an ice bath. The solution thus obtained is added over the course of 10 minutes to a solution of cuprous bromide (5.1 g.) in 48% strength aqueous hydrobromic acid (50 cc.) kept at 22°–25° C. After stirring for 1 hour at this temperature, the mixture is heated to 80°–82° C for 30 minutes. The reaction mixture is then poured into iced water (1.2 liters). The precipitate formed is filtered off, washed and then recrystallised from dimethylformamide (200 cc.). The product obtained (7 g.) is heated to 100° C with phosphorus oxychloride (70 cc.) until the evolution of gas has ceased. After cooling, the reaction mixture is poured onto ice (450 g.). The precipitate which forms is filtered off and washed with water (75 cc.), then with an 8% strength bicarbonate solution (60 cc.) and then again with water (75 cc.). This gives 6-bromo-2-(7-chloro-1,8-naphthyridin-2-yl)-3-hydroxy-1-isoindolinone (6.7 g.) melting above 260° C, with decomposition.

6-Amino-2-(7-chloro-1,8-naphthyridin-2-yl)-3-hydroxy-1-isoindolinone can be prepared in the following manner:

2-(7-Chloro-1,8-naphthyridin-2-yl)-3-hydroxy-6-nitro-1-isoindolinone (14.25 g.) in methanol (400 cc.) are hydrogenated under a pressure of 10 bars in the presence of Raney nickel (1.5 g.). The reaction mixture is filtered. The catalyst is dissolved in hydrochloric acid (d = 1.19) (20 cc.). The residual cake is dissolved in dimethylformamide (600 cc.) at about 80° C. The solution is decolorised by means of animal charcoal (2 g.) and then filtered hot. Water (1 liter) is added to the filtrate. The precipitate formed is filtered off and then washed with water (50 cc.). This gives 6-amino-2-(7-chloro-1,8-naphthyridin-2-yl)-3-hydroxy-1-isoindolinone (10.2 g.), melting above 260° C.

EXAMPLE 35

Triethylamine (16.3 g.) followed by pyridine (80 cc.) are added successively to a suspension of 6-chloro-2-(7-chloro-1,8-naphthyridin-2-yl)-3-hydroxy-1-isoindolinone (7 g.) and 1-chlorocarbonyl-4-methyl-piperazine hydrochloride (20 g.). The reaction mixture is heated for 4 hours to the reflux temperature. After cooling, methylene chloride (50 cc.) and water (100 cc.) are added. The organic phase is isolated by decantation and then washed, by decantation, successively with a normal aqueous sodium hydroxide solution (100 cc.) and then with water (100 cc.). The solution obtained is dried over magnesium sulphate and then concentrated to dryness under reduced pressure. The residue obtained is treated with ethyl acetate (50 cc.) and the insoluble product is filtered off. Recrystallisation of the latter from dimethylformamide gives 6-chloro-2-(7-chloro-1,8-naphthyridin-2-yl)-3-(4-methyl-1-piperazinyl)-carbonyloxy-1-isoindolinone (6.1 g.) melting at 256° C, with decomposition.

6-Chloro-2-(7-chloro-1,8-naphthyridin-2-yl)-3-hydroxy-1-isoindolinone can be prepared in the following manner:

A solution of silver nitrate (12.1 g.) in water (50 cc.) is added to a solution of 7-chloro-2-(5-chloro-2-dichloromethyl-benzoylamino)-1,8-naphthyridine (9.5 g.) in dimethylformamide (300 cc.) heated to a temperature of about 110° C. The reaction mixture is further heated to a temperature of about 110° C for 20 minutes and the suspension obtained is filtered hot. The filtrate obtained is poured into water (500 cc.) and the product which precipitates is filtered off. Recrystallisation from dimethylformamide gives 6-chloro-2-(7-chloro-1,8-naphthyridin-2-yl)-3-hydroxy-1-isoindolinone (5 g.) melting at 306° C.

7-Chloro-2-(5-chloro-2-dichloromethyl-benzoylamino)-1,8-naphthyridine, melting at 180° C, can be prepared by reaction of 5-chloro-2-dichloromethyl-benzoyl chloride with 2-amino-7-chloro-naphthyridine in pyridine at a temperature of about 40° C.

5-Chloro-2-dichloromethyl-benzoyl chloride can be prepared by reaction of chlorine with 5-chloro-2-methylbenzoyl chloride at a temperature of about 190° C.

5-Chloro-2-methyl-benzoyl chloride can be prepared according to the method described by R. VERBEERST et al., Bull. Soc. Chim. Belg., 77, 287 (1968).

EXAMPLE 36

1-(2-methyl-prop-2-en-1-yl)-piperazine (5.6 g.) is added all at once to a suspension of 2-(7-chloro-1,8-naphthyridin-2-yl)-3-phenoxycarbonyloxy-1-isoindolinone (3.45 g.) in acetonitrile (20 cc.). The reaction mixture is stirred for 3 hours at a temperature of about 20° C and isopropyl ether (140 cc.) is then added. The suspension obtained is stirred for 1 hour at a temperature of about 5° C and the insoluble product is then filtered off and washed with isopropyl ether (twice 20 cc.). After drying, a product (2.8 g.) is obtained, which is dissolved in methylene chloride (45 cc.). The solution obtained is then filtered through silica gel (90 g.). Thereafter elution is carried out with pure methylene chloride (1,100 cc.) followed by a mixture of methylene chloride and methanol (99.5 : 0.5 by volume) (1,250 cc.). These eluates are discarded. Elution is then carried out with a mixture of methylene chloride and methanol (99.5 : 0.5 by volume) (750 cc.) followed by a mixture of methylene chloride and methanol (99 : 1 by volume) (1,250 cc.). These eluates are combined and evaporated to dryness under reduced pressure. Recrystallisation of the residue thus obtained from acetonitrile (50 cc.) gives 2-(7-chloro-1,8-naphthyridin-2-yl)-3-[4-(2-methyl-prop-2-en-1-yl)-1-piperazinyl]-carbonyloxy-1-isoindolinone (1.9 g.) melting at 180° C.

1-(2-Methyl-prop-2-en-1-yl)-piperazine can be prepared in the following manner:

Concentrated hydrochloric acid (d = 1.19) (230 cc.) is added to a solution of anhydrous piperazine (238 g.) in absolute ethanol (600 cc.) whilst maintaining the temperature at about 30° C. The reaction mixture is heated to the reflux temperature and methallyl chloride (124.5 g.) is then added to the solution obtained. The reaction mixture is then heated to the reflux temperature for 8 hours. After cooling, the insoluble product is filtered off and washed with ethanol (3 times 200 cc.). The filtrate thus obtained is concentrated to dryness under reduced pressure. The residue is taken up in distilled water (200 cc.) and sodium hydroxide solution (d = 1.33) (200 cc.) and the solution obtained is extracted by decanting with chloroform (3 times 300 cc.). The aqueous layer is then saturated with potassium carbonate and again extracted by decanting with chloroform (twice 200 cc.). The chloroform phases are combined, dried over magnesium sulphate and then concentrated to dryness under reduced pressure. Fractional distillation under reduced pressure of the residue thus obtained gives 1-(2-methyl-prop-2-en-1-yl)-piperazine (39.5 g.) (boiling point/0.3 mm Hg = 45° C).

EXAMPLE 37

Following the procedure of Example 36 but starting from 2-(7-chloro-1,8-naphthyridin-2-yl)-3-phenoxycarbonyloxy-1-isoindolinone (4.32 g.) and 1-(but-2-en-1-yl)-piperazine (7 g.) in acetonitrile (25 cc.), 3-[4-(but-2-en-1-yl)-1-piperazinyl]-carbonyloxy-2-(7-chloro-1,8-naphthyridin-2-yl)-1-isoindolinone (1.95 g.) melting at 190° C is obtained.

1-(But-2-en-1-yl)-piperazine can be prepared as described in Example 36 but starting from anhydrous piperazine (258.4 g.), absolute ethanol (700 cc.), concentrated hydrochloric acid (d = 1.19) (250 cc.) and crotyl bromide (202 g.). This gives 1-(but-2-en-1-yl)-piperazine (110 g.) (boiling point/5.5 mm Hg = 75°–76° C).

EXAMPLE 38

Following the procedure of Example 36 but starting from 2-(7-chloro-1,8-naphthyridin-2-yl)-3-phenoxycarbonyloxy-1-isoindolinone (4.32 g.) and 1-(but-3-en-1-yl)-piperazine (7 g.) in acetonitrile (25 cc.), 3-[4-(but-3-en-1-yl)-1-piperazinyl]-carbonyloxy-2-(7-chloro-1,8-naphthyridin-2-yl)-1-isoindolinone (1.4 g.) melting at 142° C is obtained.

1-(But-3-en-1-yl)-piperazine can be prepared as in Example 36 but starting from anhydrous piperazine (12.7 g.), absolute ethanol (70 cc.), concentrated hydrochloric acid (d = 1.19) (12.8 cc.) and 4-bromo-but-1-ene (10 g.). 1-(But-3-en-1-yl)-piperazine (8.5 g.) is obtained, and can be utilised in the crude form.

EXAMPLE 39

4-Chlorocarbonyl-1-methyl-piperazine hydrochloride (9.8 g.) followed by pyridine (41 cc.) are added to a suspension of 2-(7-fluoro-1,8-naphthyridin-2-yl)-3-hydroxy-1-isoindolinone (4.89 g.) in triethylamine (9.4 cc.) and methylene chloride (100 cc.) at a temperature of between 21 and 24° C. The mixture is heated to the reflux temperature (43° C) for 2 hours and is then hydrolysed with iced water (300 g.). The organic layer is decanted and the aqueous layer is extracted with methylene chloride (600 cc.). The combined organic layers are washed with water (100 cc.) and then dried over anhydrous potassium carbonate (6 g.). After filtration and concentration, the residue is chromatographed on silica (120 g.) (0.05 – 0.2 mm). Elution is carried out using the following solvents:

| | |
|---|---|
| chloroform | 100 cc. |
| ethyl acetate | 300 cc. |
| ethyl acetate/methanol (90:10 by volume) | 400 cc. |

After evaporation of the last fractions (5 to 8), a product (3 g.) is obtained which is recrystallised from benzene (22 cc.). This gives 2-(7-fluoro-1,8-naphthyridin-2-yl)-3-(4-methyl-piperazinyl)-carbonyloxy-1-isoindolinone (1.75 g.) melting at 198°–200° C.

2-(7-Fluoro-1,8-naphthyridin-2-yl)-3-hydroxy-1-isoindolinone can be prepared in the following manner:

Sodium borohydride (1.58 g.) is added to a suspension of N-(7-fluoro-1,8-naphthyridin-2-yl)-phthalimide (11.4 g.) in a mixture of dioxane and methanol (50—50 by volume) at a temperature of 3°–4° C. After 10 minutes' reaction, the reaction mixture is poured into iced water (500 g.). The precipitate is filtered off, washed with water (120 cc.), dried and then recrystallised from toluene (280 cc.). This gives 2-(7-fluoro-1,8-naphthyridin-2-yl)-3-hydroxy-1-isoindolinone (4.6 g.) melting at 258° C.

N-(7-Fluoro-1,8-naphthyridin-2-yl)-phthalimide can be prepared in the following manner:

N-(7-Chloro-1,8-naphthyridin-2-yl)-phthalimide (15.45 g.) and silver fluoride (6.35 g.) in nitrobenzene (150 cc.) are heated to the reflux temperature for 6 hours. After cooling, the reaction mixture is diluted by adding isopropyl ether (550 cc.). The precipitate is filtered off and washed with isopropyl ether (200 cc.) and then with water (200 cc.). After drying, the dried precipitate is taken up in chloroform (2,500 cc.) and the chloroform solution is decolorised with animal charcoal (2 g.). After filtration and concentration, N-(7-fluoro-1,8-naphthyridin-2-yl)-phthalimide (11.4 g.) melting at 245° C is obtained.

EXAMPLE 40

Following the procedure of Example 28, but starting from 2-(7-chloro-1,8-naphthyridin-2-yl)-3-hydroxy-5-trifluoromethyl-1-isoindolinone (4.8 g.), 1-chlorocarbonyl-4-methyl-piperazine hydrochloride (15.1 g.), triethylamine (10.2 g. 14.2 cc.) and pyridine (66 cc.) in methylene chloride (480 cc.), a crude product (9.5 g.) is obtained, which is taken up in water (100 cc.). The precipitate is filtered off and then washed with water (60 cc.). After recrystallisation from dichloroethane (42 cc.), the product is taken up with water (37 cc.) filtered, washed and dried, 2-(7-Chloro-1,8-naphthyridin-2-yl)-3-(4-methyl-piperazinyl)-carbonyloxy-5-trifluoromethyl-1-isoindolinone (3.3 g.) melting at 222° C. is thus obtained.

2-(7-Chloro-1,8-naphthyridin-2-yl)-3-hydroxy-6-trifluoromethyl-1-isoindolinone and its isomer 2-(7-chloro-1,8-naphthyridin-2-yl)3-hydroxy-6-trifluoromethyl-1-isoindolinone can be prepared in the following manner:

Potassium borohydride (12 g.) is added at a temperature of 15°–18° C to a suspension of 5-trifluoromethyl-N-(7-chloro-1,8-naphthyridin-2-yl)-phthalimide (83.6 g.) in methanol (420 cc.) and dioxane (420 cc.). The mixture is stirred for a further 2 hours and is then cooled externally by means of an ice bath. The precipitate formed is filtered off and then washed with a mixture of methanol and dioxane (1:1 by volume) (40 cc.). The precipitate is filtered off, dried and then stirred for 30 minutes with the same mixture (200 cc.), and is then again filtered off and heated to the reflux temperature with ethanol (200 cc.). After cooling the suspension, and filtering, 2-(7-chloro-1,8-naphthyridin-2-yl)-3-hydroxy-5-trifluoromethyl-1-isoindolinone (21.9 g.) melting at a temperature above 300° C is obtained.

The solution obtained after filtering the reaction mixture and the liquid from the washes with the methanoldioxane mixture are combined. Water (2,500 cc.) is added. The precipitate which forms is filtered off, washed with water (600 cc.) and then recrystallised twice from a mixture of methanol and dioxane (5:5 by volume). This gives 2-(7-1,8-naphthyridin-2-yl)-3-hydroxy-6-trifluoromethyl-1-isoindolinone (15.3 g.) melting at 265° C.

5-Trifluoromethyl-N-(7-chloro-1,8-naphthyridin-2-yl)-phthalimide can be prepared in the following manner:

4-Trifluoromethyl-phthalic anhydride (73.5 g.) and N-hydroxysuccinimide (50.2 g.) in dimethylformamide (1,500 cc.) are heated to 75°–78° C for 18 hours. 2-Amino-7-chloro-1,8-naphthyridine (61.4 g.) and N,N'-dicyclohexylcarbodiimide (140 g.) are then added and the mixture is then heated for a further 3 hours at the same temperature. After cooling, the precipitate formed is filtered off and is washed with dimethylformamide (100 cc.) and then with isopropyl ether (200 cc.).

Water (1,500 cc.) is added to the reaction mixture. The precipitate which forms is filtered off and washed with methylene chloride (1,500 cc.). The two combined precipitates are dissolved in methylene chloride (8 liters). An insoluble material is filtered off and the filtrate is then concentrated to dryness. This gives 5-trifluoromethyl-N-(7-chloro-1,8-naphthyridin-2-yl)-phthalimide (83.6 g.) melting at 265° C.

4-Trifluoromethyl-phthalic anhydride can be prepared in the following manner:

4-Trifluoromethyl-phthalic acid (106.6 g.) and acetic anhydride (215 cc.) are heated to the reflux temperature for 30 minutes. After concentration under reduced pressure (30 mm Hg), the residue is stirred with cyclohexane (420 cc.). After filtration and drying, 4-trifluoromethyl-phthalic anhydride (73.5 g.) melting at 54° C is obtained.

4-Trifluoromethyl-phthalic acid can be prepared in the following manner:

Methyl 2-cyano-4-trifluoromethyl-benzoate (102.3 g.), sodium hydroxide pellets (108 g.), water (900 cc.) and methanol (1,900 cc.) are heated to the reflux temperature for 12 hours. The solution is decolorised by means of animal charcoal (0.6 g.). After filtration, hydrochloric acid (d = 1.19) (100 cc.) is added. The mixture is extracted with ethyl ether (2.25 liters). The organic layer is dried over anhydrous magnesium sulphate (40 g.). After filtering, and concentrating the filtrate, 4-trifluoromethyl-phthalic acid (99.1 g.) melting at 178° C is obtained.

Methyl 2-cyano-4-trifluoromethyl-benzoate can be prepared in the following manner:

Methyl 2-amino-4-trifluoromethyl-benzoate (144.6 g.) is suspended in a mixture of ice (1.3 kg.), water (730 cc.) and hydrochloric acid (d=1.19) (171.5 cc.). A solution of sodium nitrite (49.9 g.) in water (172 cc.) is added all at once to the solution obtained above. The reaction mixture is stirred for 2 hours 30 minutes at 0°–1° C and is filtered and then added dropwise, over the course of 1 hour 20 minutes, to a solution, kept at 4°–5° C, of copper sulphate (226 g.) and potassium cyanide (261 g.) in water (1,320 cc.) (the solution being prepared by the method of GABRIEL, Ber., 52, 1,089 (1919)). During the addition of the diazo compound, the pH is kept at 6–7 by adding a 10% strength solution of sodium carbonate. Stirring is continued whilst allowing the temperature to rise to 20° C. The mixture is then extracted with ether (3 liters). The ether layer is washed with water (150 cc.) and then dried over anhydrous magnesium sulphate (30 g.). After filtration and concentration, methyl 2-cyano-4-trifluoromethyl-benzoate (94.9 g.) melting at 52° C is obtained.

Methyl 2-amino-4-trifluoromethyl-benzoate can be prepared in the following manner:

2-Amino-4-trifluoromethyl-benzoic acid (141.2 g.), methanol (1.51 liters) and boron trifluoride etherate (506 cc.) are heated to the reflux temperature for 99 hours. The solution obtained is added to sodium carbonate (350 g.) in iced water (2.8 kg.). The mixture is stirred for 15 minutes and is then extracted with ethyl ether (3 liters). The ether layer is washed with water (250 cc.) and then dried over anhydrous magnesium sulphate (30 g.). After filtration and concentration, methyl 2-amino-4-trifluoromethyl-benzoate (137 g.) melting at 64° C is obtained.

2-Amino-4-trifluoromethyl-benzoic acid can be prepared by the method of HAUPTSCHEIN et al., J. Amer. Chem. Soc., (1954) 76, 1051.

EXAMPLE 41

Following the procedure of Example 28, but starting from 2-(7-chloro-1,8-naphthyridin-2-yl)-3-hydroxy-6-trifluoromethyl-1-isoindolinone (4.8 g.), 1-chlorocarbonyl-4-methyl-piperazine hydrochloride (15.1 g.), triethylamine (14.2 cc., equivalent to 10.2 g.) and pyridine (66 cc.) in methylene chloride (250 cc.), a crude product (7.8 g.) is obtained, which is triturated with water (50 cc.). The solid obtained is filtered off and washed with water (30 cc.). After recrystallisation from isopropanol (240 cc.), 2-(7-chloro1,8-naphthyridin-2-yl)-3-(4-methyl-piperazinyl)carbonyloxy-6-trifluoromethyl-1-isoindolinone (4.7 g.) melting at 219° C is obtained.

2-(7-chloro-1,8-naphthyridin-2-yl)-3-hydroxy-6-trifluoromethyl-1-isoindolinone can be prepared as described in Example 40.

The present invention includes within its scope pharmaceutical compositions comprising, as active ingredient, at least one of the naphthyridine derivatives of general formula I, or a non-toxic acid addition salt thereof, in association with a pharmaceutical carrier or coating. The invention includes especially such preparations made up for oral, parenteral or rectal administration or local application, e.g. as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or nonaqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should consititute a proportion such that a suitable dosage shall be obtained. The dosage depends on the desired therapeutic effect, on the route of administration and on the duration of the treatment. In human therapy the compositions when administered orally to an adult should generally give doses between 10 mg. and 500 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 42

Tablets containing 25 mg. of active product and having the following composition are prepared in accordance with the usual technique:

| | |
|---|---|
| 2-(7-chloro-1,8-naphthyridin-2-yl)-3-(4-methyl-piperazin-1-yl)carbonyloxy-isoindolin-1-one | 0.025 g. |
| starch | 0.090 g. |
| precipitated silica | 0.030 g. |
| magnesium stearate | 0.005 g. |

EXAMPLE 43

Tablets containing 25 mg. of active product and having the following composition are prepared in accordance with the usual technique:

| | |
|---|---|
| 6-(7-chloro-1,8-naphthyridin-2-yl)-7-(4-methylpiperazin-1-yl)carbonyloxy-5-oxo-pyrrolo[3,4-b]pyrazine | 0.025 g. |
| starch | 0.090 g. |
| precipitated silica | 0.030 g. |
| magnesium stearate | 0.005 g. |

We claim:

1. A naphthyridine derivative of the formula:

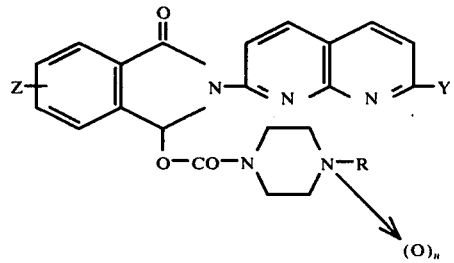

wherein Y represents hydrogen, halogen, alkyl of 1 through 4 carbon atoms, alkoxy of 1 through 4 carbon atoms, or cyano, Z represents hydrogen, halogen, alkoxy of 1 through 4 carbon atoms, nitro or trifluoromethyl, and n represents zero and R represents hydrogen, alkyl of 1 through 4 carbon atoms, alkenyl of 2 through 4 carbon atoms, alkynyl of 2 through 4 carbon atoms or hydroxyalkyl of 1 through 4 carbon atoms, or phenyl, or n represents 1 and R represents alkyl of 1 through 4 carbon atoms or hydroxyalkyl of 1 through 4 carbon atoms, and non-toxic pharmaceutically acceptable acid addition salts thereof.

2. A naphthyridine derivative according to claim 1, wherein Y is halogen or cyano, and n is O.

3. A naphthyridine derivative according to claim 1 of the formula:

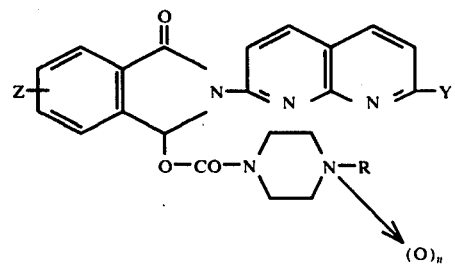

wherein Y represents hydrogen, fluorine, chlorine, bromine, methyl, methoxy or cyano, Z represents hydrogen, fluorine, chlorine, bromine, methoxy, or nitro, and (i) n represents zero and R represents hydrogen, alkyl of 1 through 4 carbon atoms, alkenyl of 2 through 4 carbon atoms, alkynyl of 2 through 4 carbon atoms, hydroxyalkyl of 1 through 4 carbon atoms or phenyl, or (ii) n represents 1 and R represents methyl, and non-toxic pharmaceutically acceptable acid addition salts thereof.

4. A naphthyridine derivative according to claim 1 of the formula:

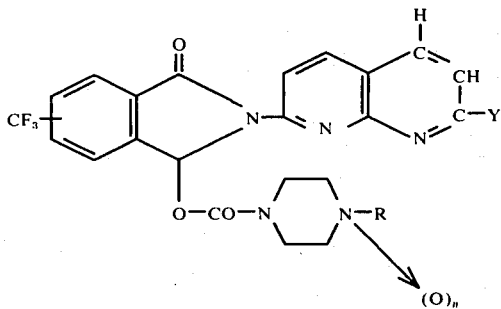

wherein Y represents hydrogen, fluorine, chlorine, bromine, methyl, methoxy or cyano, and (i) n represents zero and R represents hydrogen, alkyl of 1 through 4 carbon atoms, alkenyl of 2 through 4 carbon atoms, alkynyl of 2 through 4 carbon atoms, hydroxyalkyl of 1 through 4 carbon atoms or phenyl, or (ii) n represents 1 and R represents methyl, and non-toxic pharmaceutically acceptable acid addition salts thereof.

5. The anaphthyridine derivative according to claim 1 which is 2-(7-chloro-1,8-naphthyridin-2-yl)-3-(4-methylpiperazin-1-yl)carbonyloxy-isoindolin-1-one and non-toxic pharmaceutically acceptable acid addition salts thereof.

6. The naphthyridine derivative according to claim 1 which is 2-(7-bromo-1,8-naphthyridin-2-yl)-3-(4-methylpiperazin-1-yl)carbonyloxy-isoindolin-1-one and non-toxic pharmaceutically acceptable acid addition salts thereof.

7. The napththyridine derivative according to claim 1 which is 2-(7-cyano-1,8-naphthyridin-2-yl)-3-(4-methylpiperazin-1-yl)carbonyloxy-isoindolin-1-one and non-toxic pharmaceutically acceptable acid addition salts thereof.

8. The naphthyridine derivative according to claim 1 which is 2-(7-chloro-1,8-naphthyridin-2-yl)-3-[4-(2-hydroxyethyl)-piperazin-1-yl]carbonyloxy-isoindolin-1-one and non-toxic pharmaceutically acceptable acid addition salts thereof.

9. The naphthyridine derivative according to claim 1 which is 3-(4-allylpiperazin-1-yl)carbonyloxy-2-(7-chloro-1,8-naphthyridin-2-yl)isoindolin-1-one and non-toxic pharmaceutically acceptable acid addition salts thereof.

10. The naphthyridine derivative according to claim 1 which is 2-(7-chloro-1,8-naphthyridin-2-yl)-3-(4-ethylpiperazin-1-yl)carbonyloxy-isoindolin-1-one and non-toxic pharmaceutically acceptable acid addition salts thereof.

11. The naphthyridine derivative according to claim 1 which is 2-(7-chloro-1,8-naphthyridin-2-yl)-3-(4-propargylpiperazin-1-yl)carbonyloxy-isoindolin-1-one and non-toxic pharmaceutically acceptable acid addition salts thereof.

12. The naphthyridine derivative according to claim 1 which is 2-(7-chloro-1,8-naphthyridin-2-yl)-3-(4-t.-butylpiperazin-1-yl)carbonyloxy-isoindolin-1-one and non-toxic pharmaceutically acceptable acid addition salts thereof.

13. The naphthyridine derivative according to claim 1 which is 4-[2-(7-chloro-1,8-naphthyridin-2-yl)-3-oxo-isoindoline-1-yl]oxycarbonyl -1-methylpiperazine-1-oxide and non-toxic pharmaceutically acceptable acid addition salts thereof.

14. The naphthyridine derivative according to claim 1 which is 2-(7-chloro-1,8-naphthyridin-2-yl)-5-fluoro-3-(4-methyl-piperazinyl)-carbonyloxy-1-isoindolinone and non-toxic pharmaceutically acceptable acid addition salts thereof.

15. The naphthyridine derivative according to claim 1 which is 2-(7-chloro-1,8-nahthyridin-2-yl)-3-(4-methyl-piperazinyl)-carbonyloxy-5-nitro-1-isoindolinone and non-toxic pharmaceutically acceptable acid addition salts thereof.

16. The naphthyridin derivative according to claim 1 which is 2-(7-chloro-1,8-nahthyridin-2-yl)-5-methoxy-3-(4-methyl-piperazinyl)-carbonyloxy-1-isoindolinone and non-toxic pharmaceutically acceptable acid addition salts thereof.

17. The naphthyridine derivative according to claim 1 which is 2-(7-chloro-1,8-naphthyridin-2-yl)-3-(4-methyl-piperazinyl)-carbonyloxy-6-nitro-1-isoindolinone and non-toxic pharmaceutically acceptable acid addition salts thereof.

18. The naphthyridine derivative according to claim 1 which is 4-chloro-2-(7-chloro-1,8-naphthyridin-2-yl)-3-(4-methyl-piperazinyl)-carbonyloxy-1-isoindolinone and non-toxic pharmaceutically acceptable acid addition salts thereof.

19. The naphthyridine derivative according to claim 1 which is 7-chloro-2-(7-chloro-1,8-naphthyridin-2-yl)-3-(4-methyl-piperazinyl)-carbonyloxy-1-isoindolinone and non-toxic pharmaceutically acceptable acid addition salts thereof.

20. The naphthyridine derivative according to claim 1 which is 6-bromo-2-(7-chloro-1,8-naphthyridin-2-yl)-3-(4-methyl-piperazinyl)-carbonyloxy-1-isoindolinone and non-toxic pharmaceutically acceptable acid addition salts thereof.

21. The nahthyridine derivative according to claim 1 which is 6-chloro-2-(7chloro-1,8-naphthyridin-2-yl)-3-(4-methyl-1-piperazinyl)-carbonyloxy-1-isoindolinone and non-toxic pharmaceutically acceptable acid addition salts thereof.

22. The naphthyridin derivative according to claim 1 which is 2-(7-chloro-1,8-naphthyridin-2-yl)-3-[4-(2-methyl-prop-2-en-1-yl)-1-piperazinyl]carbonyloxy-1-isoindolinone and non-toxic pharmaceutically acceptable acid addition salts thereof.

23. The naphthyridine derivative according to claim 1 which is 3-[4-(but-2-en-1-yl)-1-piperazinyl]-carbonyloxy-2-(7-chloro-1,8-naphthyridin-2-yl)-1-isoindolinone and non-toxic pharmaceutically acceptable acid addition salts thereof.

24. The naphthyridine derivative according to claim 1 which is 3-[4-(but-3-en-1-yl)-1-piperazinyl]-carbonyloxy-2-(7-chloro-1,8-naphthyridin-2-yl)-1-isoindolinone and non-toxic pharmaceutically acceptable acid addition salts thereof.

25. The naphthyridine derivative according to claim 1 which is 2-(7-fluoro-1,8-naphthyridin-2-yl)-3-(4-methyl-piperazinyl)-carbonyloxy-1-isoindolinone and non-toxic pharmaceutically acceptable acid addition salts thereof.

26. The naphthyridine derivative according to claim 1 which is 2-(7-chloro-1,8-naphthyridin-2-yl)-3-(4-methyl-piperazinyl)-carbonyloxy-5-trifluoromethyl-1-isoindolinone and non-toxic pharmaceutically acceptable acid addition salts thereof.

27. The naphthyridine derivative according to claim 1 which is 2-(7-chloro-1,8-naphthyridin-2-yl)-3-(4-methyl-piperazinyl)carbonyloxy-6-trifluoromethyl-1-isoindolinone and non-toxic pharmaceutically acceptable acid addition salts thereof.

28. A pharmaceutical composition useful as a tranquilizer consisting essentially of, as an active ingredient, an effective amount of a naphthyridine derivative as defined in claim 5, or a non-toxic pharmaceutically acceptable acid addition salt thereof, in asosciation with a significant amount of a pharmaceutical carrier.

29. A pharmaceutical composition useful as an anticonvulsant agent consisting essentially of, as an active ingredient, an effective amount of a naphthyridine derivative as defined in claim 5, or a non-toxic pharmaceutically acceptable acid addition salt thereof, in association with a significant amount of a pharmaceutical carrier.

* * * * *